United States Patent
Tani

(10) Patent No.: US 11,006,817 B2
(45) Date of Patent: May 18, 2021

(54) ENDOSCOPE SYSTEM FOR ENDOSCOPE IMAGE PROCESSING AND IMAGE TRANSMISSION

(71) Applicant: OLYMPUS CORPORATION, Hachioji (JP)

(72) Inventor: Shinsuke Tani, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 455 days.

(21) Appl. No.: 15/947,195

(22) Filed: Apr. 6, 2018

(65) Prior Publication Data

US 2018/0220873 A1 Aug. 9, 2018

Related U.S. Application Data

(63) Continuation of application No. PCT/JP2016/079674, filed on Oct. 5, 2016.

(30) Foreign Application Priority Data

Oct. 8, 2015 (JP) .............................. JP2015-200281

(51) Int. Cl.
*A61B 1/00* (2006.01)
*A61B 1/05* (2006.01)
*A61B 1/04* (2006.01)

(52) U.S. Cl.
CPC ...... *A61B 1/00016* (2013.01); *A61B 1/00009* (2013.01); *A61B 1/00036* (2013.01);
(Continued)

(58) Field of Classification Search
CPC ....... A61B 1/041; A61B 1/00004; A61B 1/05; A61B 1/00108; A61B 1/00045; A61B 1/00036; A61B 1/00009; A61B 1/00016
See application file for complete search history.

(56) References Cited

U.S. PATENT DOCUMENTS 5,331,551 A * 7/1994 Tsuruoka ................ A61B 1/05
348/71
8,698,920 B2 * 4/2014 Uemura ............. H04N 5/23219
348/231.2
(Continued)

FOREIGN PATENT DOCUMENTS

EP 2020201 A1 * 2/2009 .......... H04N 19/186
JP 2006-121127 A 5/2006
(Continued)

OTHER PUBLICATIONS

Dec. 20, 2016 Search Report issued in International Patent Application No. PCT/JP2016/079674.

*Primary Examiner* — John P Leubecker
*Assistant Examiner* — Shankar Raj Ghimire
(74) *Attorney, Agent, or Firm* — Oliff PLC

(57) ABSTRACT

In an endoscope system, an image processing section on a processor side detects a movement amount or a distance in an image. An endoscopic-procedure-scene classifying section classify, from a feature value, to which of endoscopic procedure scene a scene of an image corresponds and further determines whether reliability of the classified endoscopic procedure scene is low. When the reliability is low, the endoscopic-procedure-scene classifying section decides a target compression ratio from an endoscopic procedure scene classified in the past, and transmits a compression parameter corresponding to the target compression ratio to a wireless endoscope. The wireless endoscope performs wireless transmission of an image compressed with the compression parameter.

7 Claims, 18 Drawing Sheets

(52) U.S. Cl.
CPC ...... *A61B 1/00045* (2013.01); *A61B 1/00108* (2013.01); *A61B 1/05* (2013.01); *A61B 1/00004* (2013.01); *A61B 1/041* (2013.01)

(56) References Cited

U.S. PATENT DOCUMENTS

| | | | | |
|---|---|---|---|---|
| 2006/0171023 | A1* | 8/2006 | Kishida | G02B 21/365 359/368 |
| 2008/0232702 | A1* | 9/2008 | Kimoto | A61B 1/041 382/232 |
| 2009/0027486 | A1* | 1/2009 | Hirakawa | A61B 1/00045 348/45 |
| 2009/0257487 | A1* | 10/2009 | Wang | H04N 19/37 375/240.02 |
| 2009/0290028 | A1* | 11/2009 | Yamasaki | H04N 5/23248 348/208.1 |
| 2009/0322865 | A1* | 12/2009 | Wang | H04N 19/105 348/68 |
| 2010/0034428 | A1* | 2/2010 | Fukunishi | G06T 7/223 382/107 |
| 2010/0214442 | A1* | 8/2010 | Uemura | H04N 5/23245 348/231.2 |
| 2011/0090056 | A1* | 4/2011 | Kawasaki | H04N 1/32037 340/10.1 |
| 2014/0063215 | A1* | 3/2014 | Miura | H04N 19/467 348/65 |
| 2014/0233826 | A1* | 8/2014 | Agaian | G16H 30/20 382/133 |
| 2018/0235527 | A1* | 8/2018 | Yamamoto | A61B 1/0002 |

FOREIGN PATENT DOCUMENTS

| | | | |
|---|---|---|---|
| JP | 2007-312810 A | 12/2007 | |
| JP | 2009-018975 A | 1/2009 | |
| JP | 2009-513283 A | 4/2009 | |
| WO | 2007/136087 A1 | 11/2007 | |
| WO | WO-2007136087 A1 * | 11/2007 | ............. H04N 19/17 |
| WO | WO-2008063565 A2 * | 5/2008 | ............... A61B 1/04 |

* cited by examiner

FIG. 7A

| IMAGE SCENE | MOVEMENT AMOUNT | ENDOSCOPIC PROCEDURE SCENE CLASSIFICATION RESULT | TARGET COMPRESSION RATIO |
|---|---|---|---|
| TRANSLATION | LARGE | PRESENCE DIAGNOSIS SCENE | MEDIUM |
| | MEDIUM | QUALITATIVE AND QUANTITATIVE DIAGNOSIS SCENE | SMALL |
| | SMALL | QUALITATIVE AND QUANTITATIVE DIAGNOSIS SCENE | SMALL |
| BACK-AND-FORTH MOVEMENT | LARGE | INSERTION SCENE | LARGE |
| | MEDIUM | PRESENCE DIAGNOSIS SCENE | MEDIUM |
| | SMALL | QUALITATIVE AND QUANTITATIVE DIAGNOSIS SCENE | SMALL |
| PARTIAL MOVEMENT | MEDIUM | TREATMENT SCENE | SMALL |
| | SMALL | | |
| OTHER THAN ABOVE | | UNCLASSIFIABLE SCENE | —(CALCULATED FROM PRECEDING FRAME) |

FIG. 7B

| SCENE ITEM | TARGET COMPRESSION RATIO | CHARACTERISTICS OF IMAGE AND IMAGE SCENE |
|---|---|---|
| INSERTION SCENE | LARGE | BACK-AND-FORTH MOVEMENT IN CASE IN WHICH MOVEMENT AMOUNT IS LARGE AND DISTANCE IS LARGE |
| PRESENCE DIAGNOSIS SCENE | MEDIUM | TRANSLATION OR BACK-AND-FORTH MOVEMENT IN CASE IN WHICH MOVEMENT AMOUNT IS MEDIUM TO LARGE AND DISTANCE IS MEDIUM TO LARGE |
| QUALITATIVE AND QUANTITATIVE DIAGNOSIS SCENE | SMALL | TRANSLATION OR BACK-AND-FORTH MOVEMENT IN CASE IN WHICH MOVEMENT AMOUNT IS SMALL TO MEDIUM AND DISTANCE IS SMALL TO MEDIUM |
| TREATMENT SCENE | SMALL | PARTIAL MOVEMENT IN CASE IN WHICH MOVEMENT AMOUNT IS SMALL TO MEDIUM AND DISTANCE IS SMALL TO MEDIUM |
| UNCLASSIFIABLE SCENE | —(PRECEDING FRAME) | MOVEMENT AMOUNT AND VALUE OF DISTANCE VARY (OR CALCULATION ACCURACY IS LOW) |

FIG.7C

| | INSERTION SCENE | | | PRESENCE DIAGNOSIS SCENE | | | QUALITATIVE AND QUANTITATIVE DIAGNOSIS SCENE | | TREATMENT SCENE | | UNCLASSIFIABLE SCENE |
|---|---|---|---|---|---|---|---|---|---|---|---|
| | MOVEMENT AMOUNT | | | MOVEMENT AMOUNT | | | MOVEMENT AMOUNT | | MOVEMENT AMOUNT | | MOVEMENT AMOUNT |
| | LARGE | MEDIUM | SMALL | LARGE | MEDIUM | SMALL | MEDIUM | SMALL | MEDIUM | SMALL | |
| TARGET COMPRESSION RATIO | LARGE | MEDIUM | SMALL | MEDIUM | SMALL | SMALL | SMALL | | SMALL | | — |

FIG.7D

| | INSERTION SCENE | | | PRESENCE DIAGNOSIS SCENE | | | QUALITATIVE AND QUANTITATIVE DIAGNOSIS SCENE | | TREATMENT SCENE | | UNCLASSIFIABLE SCENE |
|---|---|---|---|---|---|---|---|---|---|---|---|
| | DISTANCE | | | DISTANCE | | | DISTANCE | | DISTANCE | | DISTANCE |
| | LARGE | MEDIUM | SMALL | LARGE | MEDIUM | SMALL | MEDIUM | SMALL | MEDIUM | SMALL | |
| TARGET COMPRESSION RATIO | LARGE | MEDIUM | SMALL | MEDIUM | SMALL | SMALL | SMALL | | SMALL | | — |

FIG.7E

| IMAGE SCENE | MOVEMENT AMOUNT | DISTANCE | ENDOSCOPIC PROCEDURE SCENE | TARGET COMPRESSION RATIO |
|---|---|---|---|---|
| TRANSLATION | LARGE | LARGE | INSERTION SCENE | LARGE |
| | | MEDIUM | PRESENCE DIAGNOSIS SCENE | MEDIUM |
| | | SMALL | QUALITATIVE AND QUANTITATIVE DIAGNOSIS SCENE | SMALL |
| | MEDIUM | LARGE | PRESENCE DIAGNOSIS SCENE | MEDIUM |
| | | MEDIUM | QUALITATIVE AND QUANTITATIVE DIAGNOSIS SCENE | SMALL |
| | | SMALL | QUALITATIVE AND QUANTITATIVE DIAGNOSIS SCENE | SMALL |
| | SMALL | LARGE | PRESENCE DIAGNOSIS SCENE | MEDIUM |
| | | MEDIUM | QUALITATIVE AND QUANTITATIVE DIAGNOSIS SCENE | SMALL |
| | | SMALL | QUALITATIVE AND QUANTITATIVE DIAGNOSIS SCENE | SMALL |
| BACK-AND-FORTH MOVEMENT | LARGE | LARGE | INSERTION SCENE | LARGE |
| | | MEDIUM | PRESENCE DIAGNOSIS SCENE | MEDIUM |
| | | SMALL | PRESENCE DIAGNOSIS SCENE | MEDIUM |
| | MEDIUM | LARGE | INSERTION SCENE | LARGE |
| | | MEDIUM | PRESENCE DIAGNOSIS SCENE | MEDIUM |
| | | SMALL | QUALITATIVE AND QUANTITATIVE DIAGNOSIS SCENE | SMALL |
| | SMALL | LARGE | PRESENCE DIAGNOSIS SCENE | MEDIUM |
| | | MEDIUM | QUALITATIVE AND QUANTITATIVE DIAGNOSIS SCENE | SMALL |
| | | SMALL | QUALITATIVE AND QUANTITATIVE DIAGNOSIS SCENE | SMALL |
| PARTIAL MOVEMENT | | | TREATMENT SCENE | SMALL |
| OTHERS | | | UNCLASSIFIABLE SCENE | CALCULATED FROM PRECEDING FRAME |

FIG. 7F

| | INSERTION SCENE | PRESENCE DIAGNOSIS SCENE | QUALITATIVE AND QUANTITATIVE DIAGNOSIS SCENE | TREATMENT SCENE | UNCLASSIFIABLE SCENE |
|---|---|---|---|---|---|
| MOVEMENT AMOUNT | LARGE LARGE LARGE MEDIUM MEDIUM SMALL SMALL | LARGE LARGE LARGE MEDIUM MEDIUM SMALL LARGE MEDIUM MEDIUM SMALL SMALL | LARGE MEDIUM SMALL MEDIUM SMALL | LARGE MEDIUM SMALL MEDIUM SMALL | |
| DISTANCE | LARGE MEDIUM SMALL MEDIUM MEDIUM SMALL LARGE MEDIUM SMALL | LARGE LARGE MEDIUM MEDIUM MEDIUM SMALL LARGE MEDIUM MEDIUM SMALL SMALL | | | |
| TARGET COMPRESSION RATIO | LARGE LARGE MEDIUM MEDIUM MEDIUM SMALL MEDIUM SMALL SMALL SMALL | LARGE MEDIUM SMALL MEDIUM SMALL SMALL SMALL | SMALL | SMALL | — |

ENDOSCOPE SYSTEM FOR ENDOSCOPE IMAGE PROCESSING AND IMAGE TRANSMISSION

CROSS REFERENCE TO RELATED APPLICATION

This application is a continuation application of PCT/JP2016/079674 filed on Oct. 5, 2016 and claims benefit of Japanese Application No. 2015-200281 filed in Japan on Oct. 8, 2015, the entire contents of which are incorporated herein by this reference.

BACKGROUND OF THE INVENTION

1. Field of the Invention

The present invention relates to an endoscope system that wirelessly transmits an image picked up by an endoscope body including a battery to a processor.

2. Description of the Related Art

In recent years, endoscopes have been widely used in a medical field and an industrial field. As the endoscope used in the medical field, according to the progress of semiconductor technology and power saving achieved by using an LED as a light source for illumination, a battery-driven endoscope (hereinafter, endoscope body) equipped with a rechargeable battery has been put to practical use.

In an endoscope system including the endoscope body equipped with the battery in this way, cables for connecting a conventional endoscope not equipped with a battery to a processor functioning as an image processing apparatus and a light source apparatus are unnecessary. Therefore, it is possible to improve operability when a surgeon performs a surgical operation or the like (compared with when the conventional endoscope is used).

In this case, in order to secure satisfactory operability when the surgeon grips the endoscope body and preforms a surgical operation or the like, a battery capacity of the battery is limited to reduce weight of the battery equipped in the endoscope body.

In order to enable the surgeon to completely achieve a surgical operation that takes a long time period, it is necessary to further reduce power consumption in an electronic circuit equipped in the endoscope body when the endoscope body is driven by the battery.

As one of powerful methods for further reducing the power consumption in the electronic circuit equipped in the endoscope body, a method of reducing a data amount wirelessly transmitted from the endoscope body to the processor apparatus has been proposed.

In particular, since an enormous amount of data is contained in image data, if the image data is compressed and transmitted, an effect of reducing the power consumption is large.

However, when the image data is compressed, image quality is also deteriorated along with the compression. Therefore, for example, when the surgeon manipulates the endoscope body and performs a surgical operation, a high-quality image is desired in a scene in which a diseased part is closely inspected and observed. Therefore, it is desired to reduce a compression ratio or wirelessly transmit the image data without compressing the image data. In a scene in which the surgeon inserts the endoscope body in order to observe the diseased part, the surgeon does not need a high-quality image and may increase the compression ratio and wirelessly transmit the image data. In this way, it is desired to change the compression ratio of the image data and wirelessly transmit the image data according to a state of a scene in which the surgeon is about to perform an endoscopic procedure (hereinafter, an endoscopic procedure scene).

For example, Japanese Patent Application Laid-Open Publication No. 2009-18975 serving as a first conventional example discloses a capsule endoscope system including a capsule endoscope configured to photograph an inside of a subject, a receiving apparatus carried by the subject and configured to wirelessly receive and store an endoscopic image obtained by the capsule endoscope, and an information managing apparatus configured to store and manage the endoscopic image captured from the receiving apparatus and display the endoscopic image on a monitor.

Selecting means for selecting an endoscopic image stored by the information managing apparatus out of a plurality of endoscopic images wirelessly received by the receiving apparatus from the capsule endoscope calculates similarity of two endoscopic images among the plurality of endoscopic images wirelessly received by the receiving apparatus from the capsule endoscope and selects, on the basis of the calculated similarity, an endoscopic image wirelessly transmitted from the receiving apparatus to the information managing apparatus to thereby enable image reading of the endoscopic image photographed by the capsule endoscope to be quickly performed.

Japanese Patent Application Laid-Open Publication No. 2009-513283 serving as a second conventional example discloses a capsule camera apparatus and describes that the capsule camera apparatus includes a housing suitable for swallowing, a light source in the housing, a camera for capturing a first digital image and a second digital image of a region irradiated by the light source, a movement detector configured to detect a movement on the basis of a difference between the first digital image and the second digital image, and a movement evaluator configured to designate, on the basis of a measurement amount of the movement, a second digital image to be further processed, and a capture rate for the capturing is changed according to the movement detection.

SUMMARY OF THE INVENTION

An endoscope system according to an aspect of the present invention includes: an endoscope body configured to be inserted into a subject and including an image pickup section provided at a distal end portion and a first wireless transmission section configured to wirelessly transmit an image signal picked up by the image pickup section; a processor including a second wireless transmission section arranged on an outside of the subject and configured to receive a wirelessly-transmitted image signal and an image processing section configured to perform image processing of the wirelessly-transmitted image signal; a scene classifying section configured to classify, on the basis of an image signal obtained by picking up an image of a region in the subject with the image pickup section, to which endoscopic procedure scene in a plurality of representative endoscopic procedure scenes a scene of an image for observing the region by the endoscope body corresponds; a scene-reliability determining section configured to perform determination of reliability of the scene classified by the scene classifying section; and an image-signal-target-compression-ratio deciding section configured to, when the scene-reliability determining section determines that the reliability of the scene classified by the scene classifying section is low, decide, according to a classification result of a scene by the scene classifying section in an image signal of a frame preceding, by a predetermined period, a frame of the image signal, the reliability of which is determined as low, a target compression ratio of the image signal wirelessly transmitted by the first wireless transmission section.

BRIEF DESCRIPTION OF THE DRAWINGS

FIG. 7A is a diagram showing, in a table format, an example of endoscopic procedure scenes classified by image scenes and magnitudes of movement amounts and target compression ratios set for the respective endoscopic procedure scenes;

FIG. 7B is a diagram showing, in a table format, a relation between target compression ratios set according to endoscopic procedure scenes and characteristics of images and image scenes;

FIG. 7C is a diagram showing, in a table format, a relation between endoscopic procedure scenes and target compression ratios set according to movement amounts and stored in an LUT;

FIG. 7D is a diagram showing, in a table format, a relation between endoscopic procedure scenes and target compression ratios set according to distances and stored in the LUT;

FIG. 7E is a diagram showing, in a table format, a relation between endoscopic procedure scenes classified according to image scenes, movement amounts, and distances and target compression ratios set according to the endoscopic procedure scenes;

FIG. 7F is a diagram showing, in a table format, a relation between endoscopic procedure scenes and target compression ratios set according to movement amounts and distances;

DETAILED DESCRIPTION OF THE PREFERRED EMBODIMENT

An embodiment of the present invention is explained below with reference to the drawings.

First Embodiment

Figure 1:
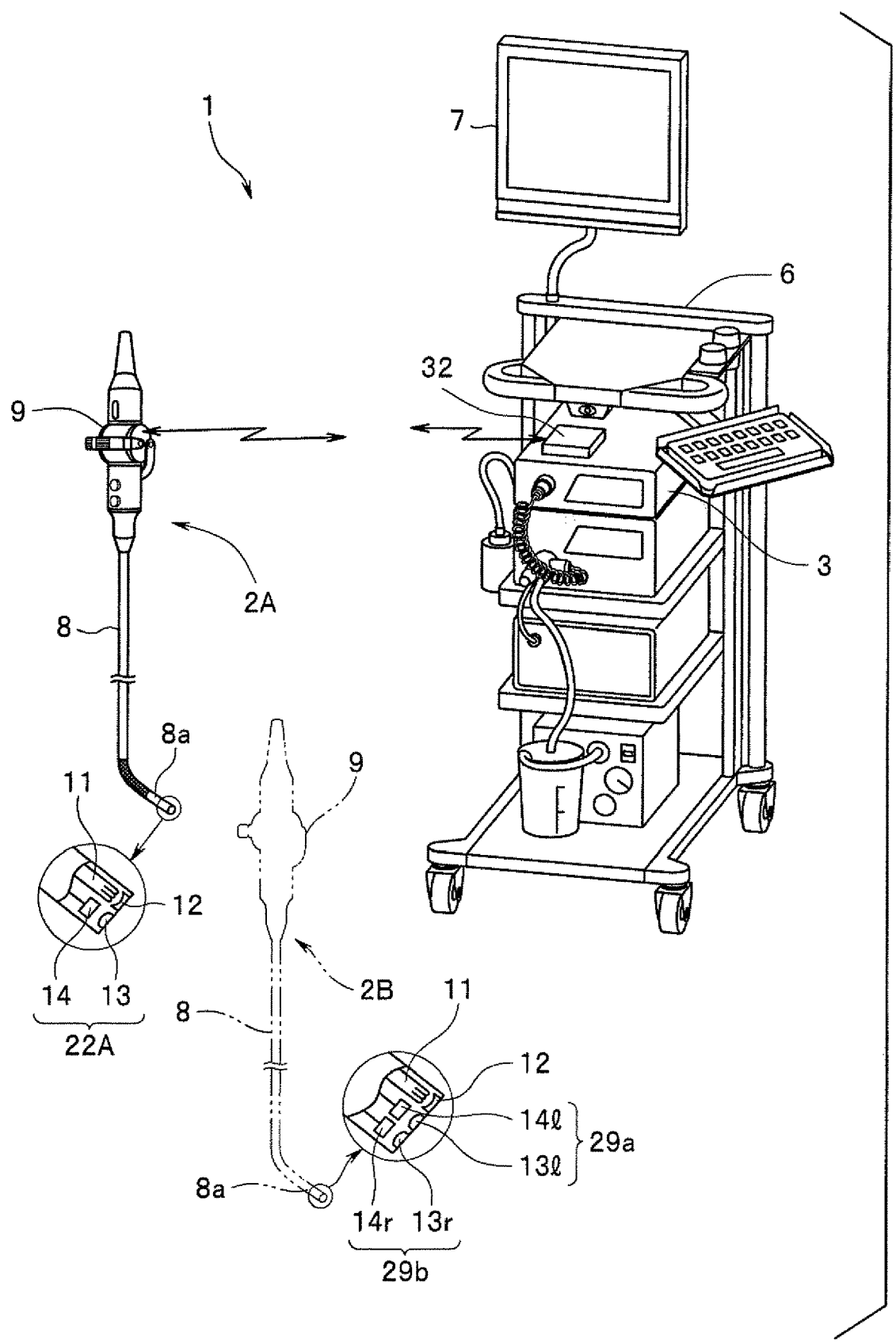
FIG. 1 is a diagram showing an overall configuration of an endoscope system according to a first embodiment of the present invention.

As shown in FIG. 1, a main part of an endoscope system 1 is configured by a wireless endoscope body (hereinafter abbreviated as wireless endoscope) 2A forming a battery-driven portable endoscope, a processor 3 wirelessly connected to the wireless endoscope 2A and configured to perform predetermined image processing, a monitor 7 functioning as a display apparatus connected to the processor 3 and configured to display an endoscopic image and the like, and the like. In the endoscope system 1 according to the embodiment, besides the wireless endoscope 2A including a single image pickup device, a wireless endoscope 2B indicated by an alternate long and short dashes lines including two image pickup devices for enabling stereoscopic vision can also be used.

Note that, when the endoscope system 1 according to the embodiment is used in an operating room, various medical apparatuses such as the processor 3, for example, apparatuses such as an electric knife apparatus, a pneumoperitoneum apparatus, and a video recorder and a gas cylinder filled with carbon dioxide are placed on a cart 6.

A wireless endoscope 2I (I=A or B) includes an elongated insertion section 8 inserted into a body cavity and an operation section 9 provided on a proximal end side of the insertion section 8.

Figure 2:
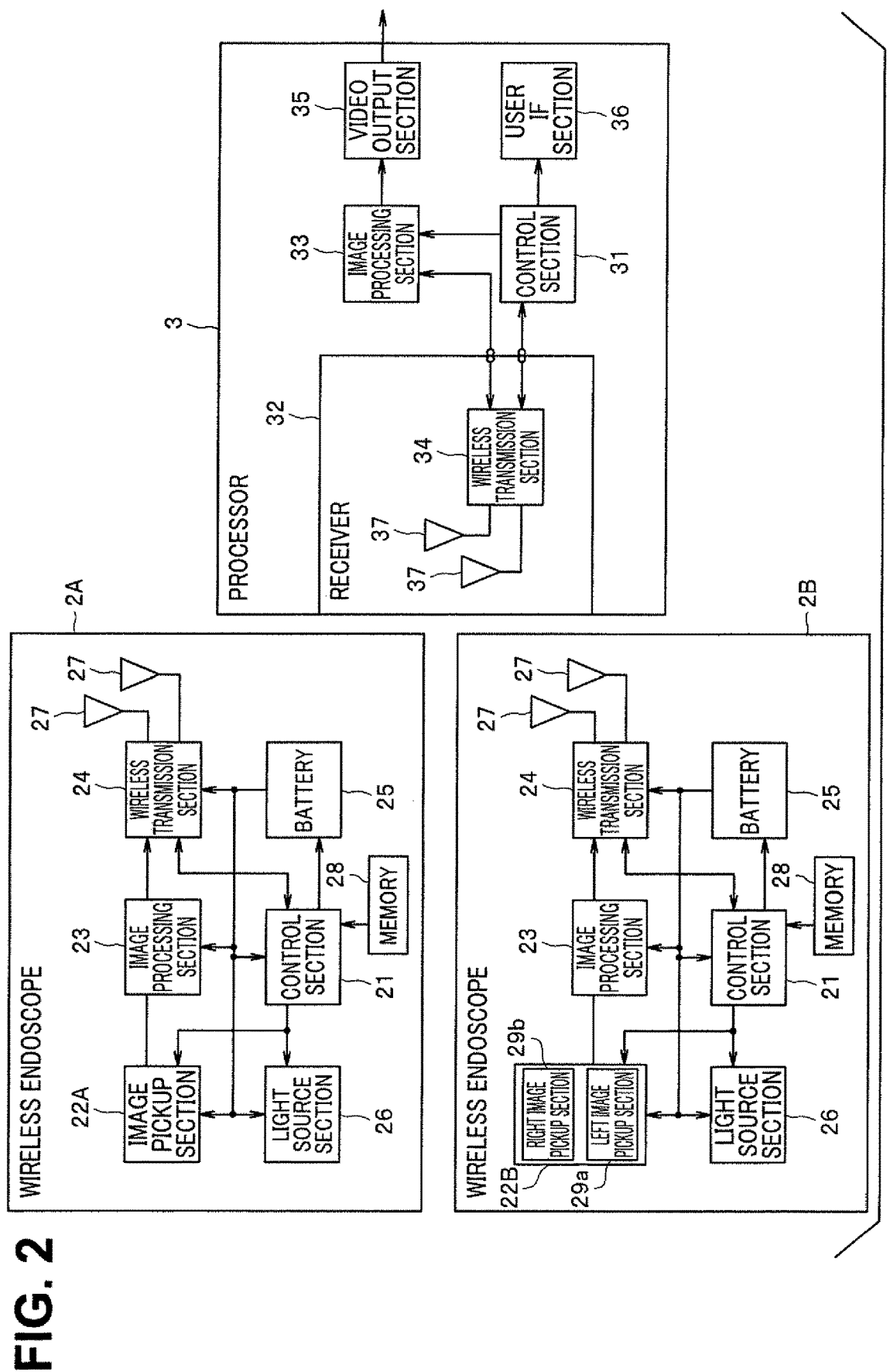
FIG. 2 is a block diagram showing configurations of wireless endoscopes functioning as endoscope bodies and a processor in the endoscope system according to the first embodiment.

A light source section (or a light source unit) 26 configured by a not-shown light emitting diode provided in the wireless endoscope 2I as shown in FIG. 2 is disposed in the operation section 9. The light source section 26 is controlled by an endoscope-side control section 21 to generate illumination light for illuminating inside of the body cavity. The illumination light is guided to a distal end portion 8a provided at a distal end of the insertion section 8 by a light guide 11 shown in an enlarged view in FIG. 1 and irradiates a region (referred to as object as well) such as a diseased part in the subject via an illumination lens 12 provided in an illumination window of the distal end portion 8a. As shown in the enlarged view, image pickup sections 22A and 22B are provided at the distal end portion 8a.

The image pickup section 22A is configured by an objective lens 13 disposed at the distal end portion 8a of the insertion section 8 and configured to form an optical image of the object and an image pickup device 14 such as a charge coupled device (CCD) or a CMOS sensor arranged in a position of the image formation. An image of a return light from the object by the illumination light emitted from the light source section 26 is formed on an image pickup surface of the image pickup device 14. The image pickup device 14 outputs, with photoelectric conversion, a picked-up image (signal) based on an object optical image to an endoscope-side image processing section (simply referred to as image processing section as well) 23. Note that (the image pickup device 14 of) the image pickup section 22A may be defined as outputting (or generating) the picked-up image (signal). The image processing section 23 may be defined as generating an image (a signal) obtained by performing image processing on the picked-up image (signal). (The image pickup device 14 of) the image pickup section 22A may be defined as outputting (or generating) an image (a signal). The image processing section 23 may be defined as performing the image processing on the image (the signal) and generating an image (a signal) subjected to the image processing. The same applies to the image pickup section 22B.

Figure 3:
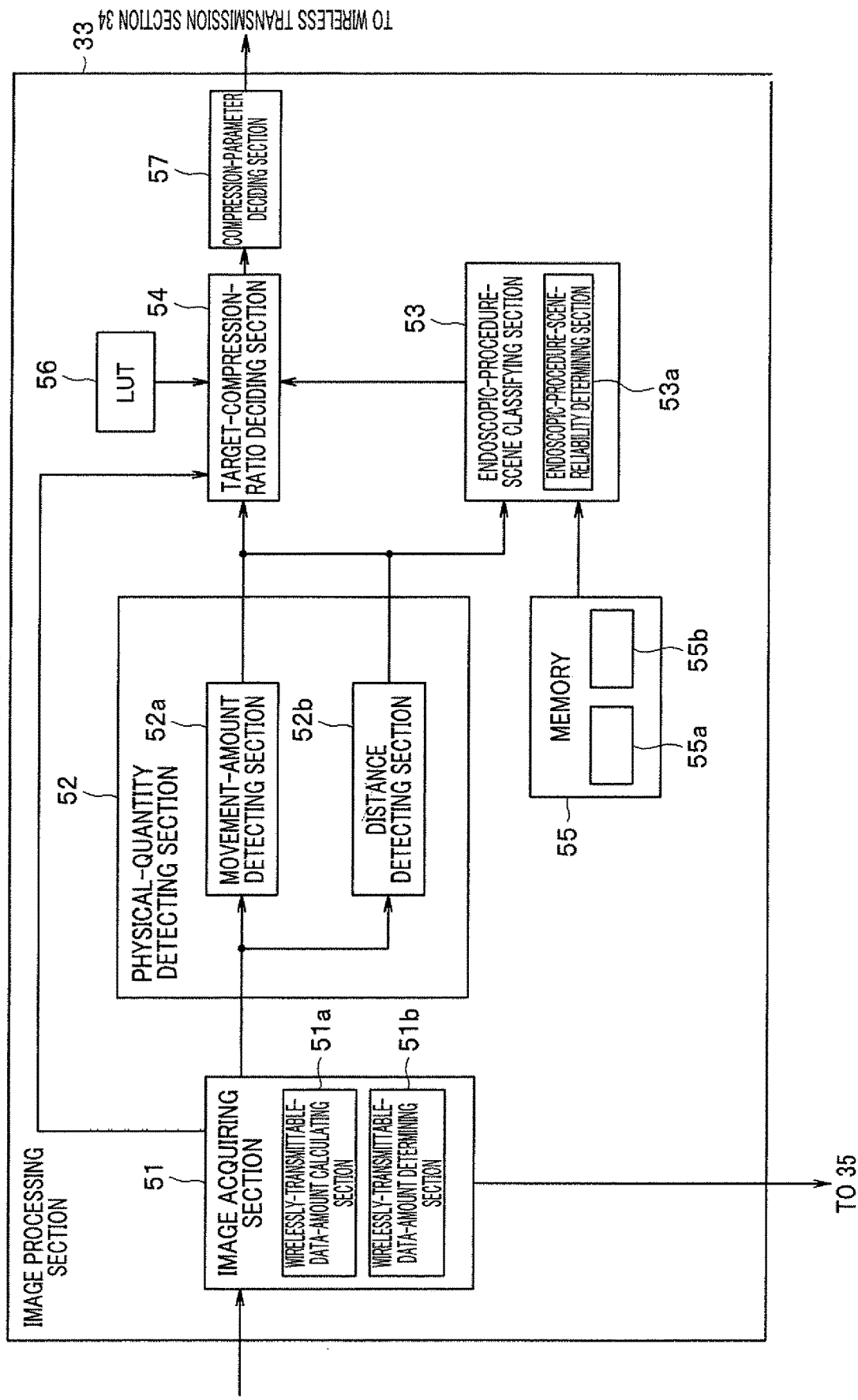
FIG. 3 is a block diagram showing a configuration of an image processing section on the processor side in the endoscope system according to the first embodiment.

FIG. 2 shows configurations of the wireless endoscopes 2A and 2B and the processor 3 in the endoscope system 1 according to the first embodiment. FIG. 3 shows a configuration of an image processing system in the processor 3.

As shown in FIG. 2, the wireless endoscope 2A in the embodiment is a battery-driven portable endoscope adopting a wireless configuration wirelessly connected to the processor 3. A main part of the wireless endoscope 2A is configured by an endoscope-side control section (hereinafter referred to as control section as well) 21 configured to control respective circuit sections in the wireless endoscope 2A, an image pickup section 22A including a single image pickup device configured to acquire a picked-up image of a region in a subject, an endoscope-side image processing section 23 configured to apply predetermined image processing to the picked-up image or a picked-up image signal outputted from the image pickup section 22A, an endoscope-side wireless transmission section (simply referred to as wireless transmission section as well) 24 for wirelessly transmitting a predetermined signal between the endoscope-side wireless transmission section 24 and the processor 3, a battery 25 configured to supply electric power to the respective sections of the wireless endoscope 2A, a light source section 26 for irradiating an inside of a body cavity, and an antenna 27 for performing wireless transmission and reception between the antenna 27 and the processor 3.

Note that the control section 21 is configured by, for example, a central processing unit (abbreviated as CPU) configured to perform a control operation according to a program. The image processing section 23 is configured by an image processing circuit including a CDS circuit configured to perform correlated double sampling (CDS) processing on an image pickup signal outputted from the image pickup section 22A. The wireless transmission section 24 is configured by a wireless transmission circuit configured to generate a transmission signal to be wirelessly transmitted and a wireless reception circuit configured to receive the wirelessly-received transmission signal and generate a demodulated signal. Note that the control section 21, the image processing section 23, and the like may be configured by a digital signal processor (DSP). A control section 31, an image processing section 33, and the like on the processor 3 side explained below may also be configured by a CPU or a DSP.

The wireless endoscope 2A includes a memory 28 configured to store peculiar identification information (abbreviated as ID) including a type of the wireless endoscope 2A. When wirelessly transmitting a signal to the processor 3, the wireless endoscope 2A transmits the signal with the ID attached to the signal. Therefore, when wirelessly receiving the signal, the processor 3 can identify the wireless endoscope 2A functioning as a transmission source.

The battery 25 can be mounted on the operation section 9. After being mounted on the wireless endoscope 2A, the battery 25 can function as a power supply section and supply electric power to the image pickup section 22A, the endoscope-side image processing section 23, the light source section 26, and the endoscope-side wireless transmission section 24 besides the endoscope-side control section 21.

The endoscope-side control section 21 controls the respective circuit sections in the wireless endoscope 2A and controls the battery 25, which is the power supply section, to supply electric power to the respective sections.

The endoscope-side control section 21 acquires a compression parameter serving as information related to a target compression ratio transmitted from the processor 3 side via the endoscope-side wireless transmission section 24 and controls the endoscope-side image processing section 23 on the basis of the compression parameter.

The endoscope-side image processing section 23 is controlled by the endoscope-side control section 21 to apply, to a picked-up image outputted from the image pickup section 22A, predetermined image processing for compressing the picked-up image to a target compression ratio according to the compression parameter and thereafter output the picked-up image to the endoscope-side wireless transmission section 24.

The endoscope-side wireless transmission section 24 is controlled by the endoscope-side control section 21 to wirelessly perform transmission and reception of image data and predetermined communication data via the antenna 27 between the endoscope-side wireless transmission section 24 and the processor 3. In the embodiment, the endoscope-side wireless transmission section 24 is capable of performing, for example, wireless communication by a 60 GHz band and wireless communication by a 5 GHz band.

The wireless endoscope 2B includes, instead of the image pickup section 22A in the wireless endoscope 2A, an image pickup section 22B configured of a left image pickup section 29a and a right image pickup section 29b arranged on the left and right. Otherwise, the wireless endoscope 2B has the same configuration as the configuration of the wireless endoscope 2A.

That is, objective lenses 13l and 13r are arranged in a left-right direction as shown in an enlarged view in FIG. 1. Image pickup devices 14l and 14r are respectively arranged in respective image forming positions of the objective lenses 131 and 13r. The left image pickup section 29a configured by the objective lens 131 and the image pickup device 141 and the right image pickup section 29b configured by the objective lens 13r and the image pickup device 14r are formed.

The image processing section 23 in the wireless endoscope 2B applies predetermined image processing to left and right picked-up images generated by the left image pickup section 29a and the right image pickup section 29b. The wireless transmission section 24 in the wireless endoscope 2B wirelessly transmits the left and right picked-up images generated by the image processing section 23. In the case of the wireless endoscope 2B, an ID including information concerning a type of stereoscopic vision is transmitted to the processor 3. Therefore, the processor 3 performs image processing corresponding to the stereoscopic wireless endoscope 2B.

As explained below, in the stereoscopic wireless endoscope 2B, when an image of a region such as a diseased part in a subject is picked up, it is possible to calculate a distance between the image pickup section 22B or the distal end portion 8a and the region from information concerning two-dimensional positions of the left and right image pickup devices.

As wireless communication between the wireless endoscope 2I and the processor 3 in the embodiment, for example, wireless communication using a 60 GHz band is performed concerning an image signal outputted from the image processing section 23 and wireless communication using a 5 GHz band is performed concerning communication related to information such as a compression ratio. Note that a scheme for performing the wireless communication of both of the image signal and the information such as the compression ratio at 5 GHz, a scheme for performing the wireless communication of both of the image signal and the information such as the compression ratio at 60 GHz, or a combination of other compression schemes may be adopted. As explained below, the wireless communication of the image signal and information such as a compression parameter may be dividedly performed at 60 GHz and 5 GHz.

Consequently, the endoscope-side wireless transmission section 24 is controlled by the control section 21 to sequentially wirelessly transmit an image signal obtained by image pickup to the processor 3 via the antenna 27 according to the compression ratio and receive, at a predetermined time interval, via the antenna 27, the information concerning the compression parameter transmitted from the processor 3.

On the other hand, in the embodiment, as shown in FIG. 2, a main part of the processor 3 is configured by a processor-side control section (simply referred to as control section as well) 31 configured to control the respective circuit sections in the processor 3, a wireless receiver 32 for wirelessly performing transmission of information to the wireless endoscope 2I, a processor-side image processing section (simply referred to as image processing section as well) 33 configured to apply predetermined processing to an image pickup signal of an image pickup section 22I acquired via the wireless receiver 32, a video output section 35 configured to convert a picked-up image outputted from the processor-side image processing section 33 into a format displayable on the monitor 7 and output the picked-up image, and a user IF section 36, which is an interface configured to receive operation by a user such as a surgeon.

A main part of the wireless receiver 32 is configured by a processor-side wireless transmission section (simply referred to as wireless transmission section as well) 34 for wirelessly transmitting a predetermined signal between the wireless receiver 32 and the wireless endoscope 2I and an antenna 37 for wireless transmission and reception to and from the wireless endoscope 2I.

Note that, in the embodiment, the wireless receiver 32 is configured separately from a processor body and connected to the processor 3 body by a not-shown connector. In FIG. 1, a state is shown in which the wireless receiver 32 configured separately from the body of the processor 3 is placed on the processor 3 on the cart 6.

The processor-side wireless transmission section 34 in the wireless receiver 32 is controlled by the processor-side control section 31 to wirelessly perform transmission and reception of image data and predetermined communication data between the processor-side wireless transmission section 34 and the wireless endoscope 2I via the antenna 37. In the embodiment, like the endoscope-side wireless transmission section 24, the processor-side wireless transmission section 34 is capable of performing, for example, the wireless communication by the 60 GHz band and the wireless communication by the 5 GHz band.

That is, concerning an image signal of the image processing section 23 transmitted from the wireless endoscope 2I, the processor-side wireless transmission section 34 sequentially receives the image signal with the wireless communication using the 60 GHz band via the antenna 37. Concerning communication related to information such as a compression parameter determined in the processor 3, the processor-side wireless transmission section 34 transmits the information to the wireless endoscope 2I with the wireless communication using the 5 GHz band at a predetermined time interval via the antenna 37.

The user IF section 36 is an interface configured to receive user operation and is configured by, for example, a front panel and various buttons of a control system. The user IF section 36 outputs an operation signal based on the user operation to the processor-side control section 31.

Various kinds of user operation such as designation of an observation mode of the wireless endoscope 2I and setting concerning image display can be received by the user IF section 36. The processor-side control section 31 is capable of giving, on the basis of an operation signal outputted from the user IF section 36, various instructions to the endoscope-side control section 21 of the wireless endoscope 2I via the processor-side wireless transmission section 34. Note that the processor 3 may be configured to incorporate the processor-side wireless transmission section 34.

The processor-side image processing section 33 in the processor 3 is explained in detail.

FIG. 3 shows a configuration of an image processing section (the processor-side image processing section 33) of the processor 3 in the endoscope system 1 according to the first embodiment.

As shown in FIG. 3, a main part of the processor-side image processing section 33 is configured by an image acquiring section (or an image acquisition circuit) 51 configured to acquire an image signal wirelessly transmitted from the wireless endoscope 2I via the processor-side wireless transmission section 34, a physical-quantity detecting section (or a physical-quantity detection circuit) 52 configured to detect, on the basis of the image signal acquired in the image acquiring section 51, a physical quantity reflecting a state of observation of a region in a subject by the image pickup section 22A or 22B provided at the distal end portion 8a of the insertion section 8 in the wireless endoscope 2I, an endoscopic-procedure-scene classifying section (or an endoscopic-procedure-scene classification circuit) 53 configured to classify, on the basis of a feature value of the physical quantity detected in the physical-quantity detecting section 52, to which representative endoscopic procedure scene of a plurality of representative endoscopic procedure scenes prepared or registered in advance in a scene in which the surgeon is performing a procedure using the wireless endoscope 2I corresponds, a target-compression-ratio deciding section (or a target-compression-ratio decision circuit) 54 configured to decide, from the endoscopic procedure scene classified in the endoscopic-procedure-scene classifying section 53 and the feature value of the physical quantity (more specifically, magnitude of the physical quantity, a distribution of the physical quantity in a plurality of positions, etc.) acquired in the physical-quantity detecting section 52, a target compression ratio of an image used in the endoscope-side image processing section 23 in the wireless endoscope 2I, and a compression-parameter deciding section (or a compression-parameter decision circuit) 57 configured to decide a compression parameter for compression to the decided target compression ratio.

Note that, when the wirelessly-transmitted image signal is compressed, the image acquiring section 51 performs image processing for expanding the image signal and generates an uncompressed image signal. The image signal is outputted to the physical-quantity detecting section 52 and the video output section 35. The image acquiring section 51 includes a wirelessly-transmittable-data-amount calculating section 51a configured to grasp a state of wireless transmission and calculate a wirelessly transmittable data amount and a wirelessly-transmittable-data-amount determining section 51b configured to determine the wirelessly transmittable data amount. Note that an example is shown in which the wirelessly-transmittable-data-amount calculating section 51a and the wirelessly-transmittable-data-amount determining section 51b are provided on an inside of the image acquiring section 51. However, the wirelessly-transmittable-data-amount calculating section 51a and the wirelessly-transmittable-data-amount determining section 51b may be provided on the outside of the image acquiring section 51.

The wirelessly transmittable data amount calculated by the wirelessly-transmittable-data-amount calculating section 51a and a result of the determination by the wirelessly-transmittable-data-amount determining section 51b are sent to the target-compression-ratio deciding section 54. The target-compression-ratio deciding section 54 prioritizes the wirelessly transmittable data amount to decide a target compression ratio in wirelessly transmitting the image signal.

As explained below, a wirelessly transmittable data amount is calculated and determined and, when an image signal in the case of a low target compression ratio is wirelessly transmitted, a compression ratio of the image signal is set to be equal to or smaller than the wirelessly transmittable data amount to enable the image signal to be surely wirelessly transmitted.

The physical-quantity detecting section 52 in the embodiment includes a movement-amount detecting section (or a movement-amount detection circuit) 52a configured to detect, on the basis of an image signal obtained by picking up an image of the inside of the subject with the image pickup section 22A or 22B, movement amounts (or movement vectors) in a plurality of representative regions in an image for one frame as the physical quantity and a distance detecting section (or the distance detection circuit) 52b configured to detect, for example, a plurality of distances between a plurality of positions in the subject, an image of which is picked up by the image pickup section 22B, and the image pickup section 22B as the physical quantity. Note that the plurality of representative regions where the movement amounts are detected are a plurality of representative positions when the plurality of representative regions are the smallest. The plurality of respective positions where the distances are detected may be a plurality of respective representative regions serving as an aggregate of positions.

In the embodiment, when the wireless endoscope 2B including the image pickup section 22B capable of giving stereoscopic vision is used, for example, it is possible to select, from the user IF section 36, one of the movement amount detected by the movement-amount detecting section 52a and the distance detected by the distance detecting section 52b as the physical quantity detected in the physical-quantity detecting section 52 and perform classification of an endoscopic procedure scene from an image scene. On the other hand, when the wireless endoscope 2A including the image pickup section 22A configured of one image pickup device is used, the movement amount detected by the movement-amount detecting section 52a is selected as the physical quantity detected in the physical-quantity detecting section 52 to perform the classification of the endoscopic procedure scene. In a specific example of operation explained below, when the wireless endoscope 2A is used, the movement-amount detecting section 52a is automatically selected according to an ID.

Note that, in a wireless endoscope (2C) of a type including a laser light source for distance measurement and a measuring section configured to measure a time period until laser light irradiated on the subject side returns, even in a wireless endoscope including the image pickup section 22A configured of one image pickup device, as in the case in which the wireless endoscope 2B including the image pickup section 22B capable of giving stereoscopic vision, it is possible to select one of the movement amount detected by the movement-amount detecting section 52a and the distance detected by the distance detecting section 52b as the physical quantity detected in the physical-quantity detecting section 52 and perform classification of the endoscopic procedure scene. In the following explanation, for simplification, an example is explained in which a wireless endoscope is the wireless endoscopes 2A and 2B. However, the explanation can be applied to the wireless endoscope 2C as well.

The endoscopic-procedure-scene classifying section 53 in the embodiment further has, besides performing the classification of the endoscopic procedure scene on the basis of the feature value of the physical quantity detected by the physical-quantity detecting section 52 as explained above, a function of an endoscopic-procedure-scene-reliability determining section (or a scene-reliability determination circuit) 53a configured to perform determination of reliability of the classified endoscopic procedure scene.

In FIG. 3, the configuration is shown in which the endoscopic-procedure-scene classifying section 53 includes the endoscopic-procedure-scene-reliability determining section 53a. However, a configuration may be adopted in which the endoscopic-procedure-scene-reliability determining section 53a is provided on an outside of the endoscopic-procedure-scene classifying section 53.

The image processing section 33 includes a memory 55 including a representative-endoscopic-procedure-scene-feature-value storing section 55a having stored feature values representing a representative plurality of endoscopic procedure scenes at the time when the endoscopic-procedure-scene classifying section 53 performs the classification of the endoscopic procedure scene. The endoscopic-procedure-scene classifying section 53 performs the classification of the endoscopic procedure scene referring to information of the representative-endoscopic-procedure-scene-feature-value storing section 55a in the memory 55 (see, for example, FIG. 7A and FIG. 7B).

The endoscopic-procedure-scene classifying section 53 stores information concerning endoscopic procedure scenes classified over time (in time order), for example, by an appropriate number of frames (retroactively to the past from an image of a present frame) in the classified-scene storing section 55b in the memory 55.

When determining that reliability of the endoscopic procedure scene classified by the endoscopic-procedure-scene classifying section 53 is low, the endoscopic-procedure-scene-reliability determining section 53a sends, to the target-compression-ratio deciding section 54, a classification result of the endoscopic procedure scene classified by the endoscopic-procedure-scene classifying section 53 and stored in the classified-scene storing section 55b in an image (a signal) of a frame preceding, by a predetermined period, an image (a signal) of a frame, reliability of which is determined as low.

In an endoscopic procedure scene, reliability of which is not determined as low by the endoscopic-procedure-scene-reliability determining section 53a, the target-compression-ratio deciding section 54 decides a target compression ratio according to the classification result of the endoscopic procedure scene classified by the endoscopic-procedure-scene classifying section 53, the magnitude of the physical quantity, and the like (see FIG. 7A, FIG. 7B, and FIG. 7C). As explained above, the wirelessly transmittable data amount and the determination result are inputted to the target-compression-ratio deciding section 54. Therefore, the target-compression-ratio deciding section 54 decides the target compression ratio to set a data amount of a wirelessly-transmitted image signal at least within a range of a data amount equal to or smaller than the wirelessly transmittable data amount. In other words, the target-compression-ratio deciding section 54 decides the target compression ratio according to the wirelessly transmittable data amount, the classification result of the endoscopic procedure scene, the magnitude of the physical quantity, and the like. In that case, the target-compression-ratio deciding section 54 prioritizes the wirelessly transmittable data amount.

The target-compression-ratio deciding section 54 decides the target compression ratio referring to information stored in a lookup table (abbreviated as LUT) 56 prepared in advance (see FIG. 7C and FIG. 7D).

The physical-quantity detecting section 52 includes the movement-amount detecting section 52a configured to detect a movement amount and the distance detecting section 52b configured to detect a distance. Classification of an endoscopic procedure scene is performed on the basis of an image scene and the detected movement amount or the detected distance. Therefore, first, the detection of a movement amount by the movement-amount detecting section 52a and discrimination of an image scene are explained. That is, the endoscopic-procedure-scene classifying section 53 classifies an endoscopic procedure scene from the image scene. Note that the endoscopic-procedure-scene classifying section 53 may perform the classification of the endoscopic procedure scene not through the discrimination of the image scene.

Figure 4:
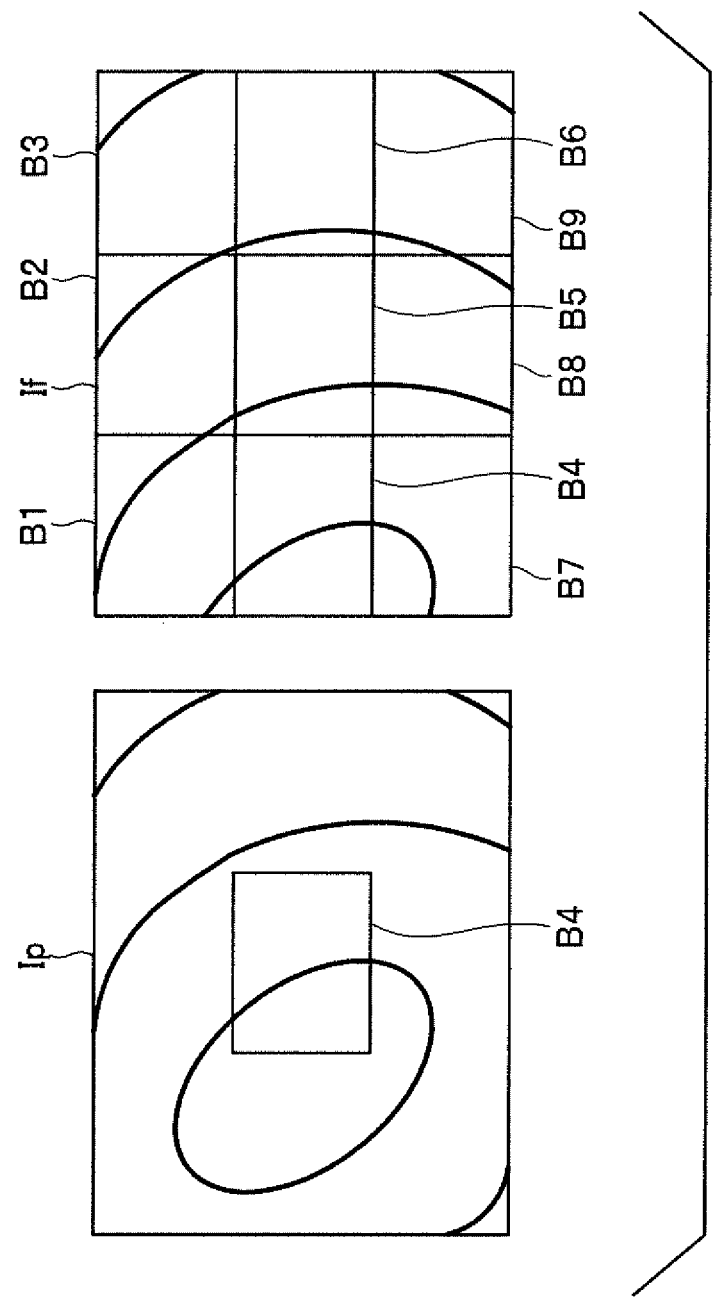
FIG. 4 is an explanatory diagram of a case in which a region of one image corresponding to a divided region in the other image is detected by block matching for calculating a movement amount with a movement detecting section.

FIG. 4 shows an image (a signal) Ip of a present frame picked up by the image pickup section 22I and inputted to the movement-amount detecting section 52a of the image processing section 33 of the processor 3 and an image (a signal) If of an immediately preceding frame.

The movement-amount detecting section 52a divides both the images Ip and If into a plurality of segmented blocks (or segmented regions) Bi (in FIG. 4, i=1 to 9) and performs processing of block matching for determining with an image of which block Bi in the image If an image of one block B5 in the image Ip coincides most as shown in FIG. 4.

In the case of FIG. 4, as the processing of the block matching, the movement-amount detecting section 52a calculates a sum of squares of differences of corresponding pixel values between the blocks B5 and Bi (SSD: sum of squared difference) and the like and determines that the block Bi, in which the SSD is a minimum, is a same block matching the block B5.

For example, in FIG. 4, when the block B5 in the image Ip matches the block B4 in the image Ip most, the movement-amount detecting section 52a detects, as a movement amount in one frame period, a movement amount from a representative position (simply referred to as position as well) of a center position or the like of the block B5 to a representative position of the block B4.

The movement-amount detecting section 52a detects a movement amount in blocks from the blocks B1 to B9 in the image Ip. In FIG. 4, the detection of the movement amount in the case of nine blocks B1 to B9 is explained. However, actually, the movement-amount detecting section 52a detects a movement amount in blocks divided in a larger number of divisions (in other words, blocks or regions having a small size).

Figure 5A:
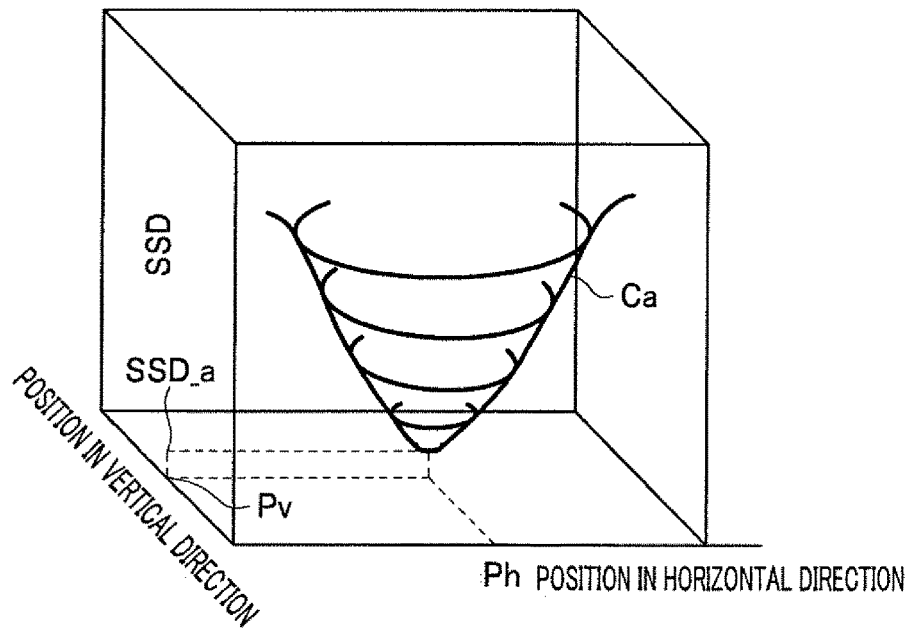
FIG. 5A is a diagram showing a distribution of an SSD with respect to displacement in a horizontal direction and displacement in a vertical direction calculated by the block matching shown in FIG. 4.

FIG. 5A shows an example of a characteristic Ca of an SSD calculated in the images Ip and If when the sizes of the block in FIG. 4 is set small and positions in a horizontal direction and a vertical direction. For example, FIG. 5A shows a characteristic of the SSD in the case in which, near a corresponding position (corresponding to a position on the image Ip side) on the image If side, the position is changed with respect to a position on the image Ip side (therefore, the characteristic corresponds to a characteristic for deciding a movement amount).

In the example shown in FIG. 5A, the characteristic is a characteristic in which the SSD is a minimum value SSD_a in a position Ph in the horizontal direction and a position Pv in the vertical direction and the SSD increases in a parabola shape when the SSD deviates from the positions Ph and Pv.

In the case of such a characteristic Ca, in a detection result of a movement amount by the block matching, it is at least regarded (evaluated) that reliability is not low.

Figure 5B:
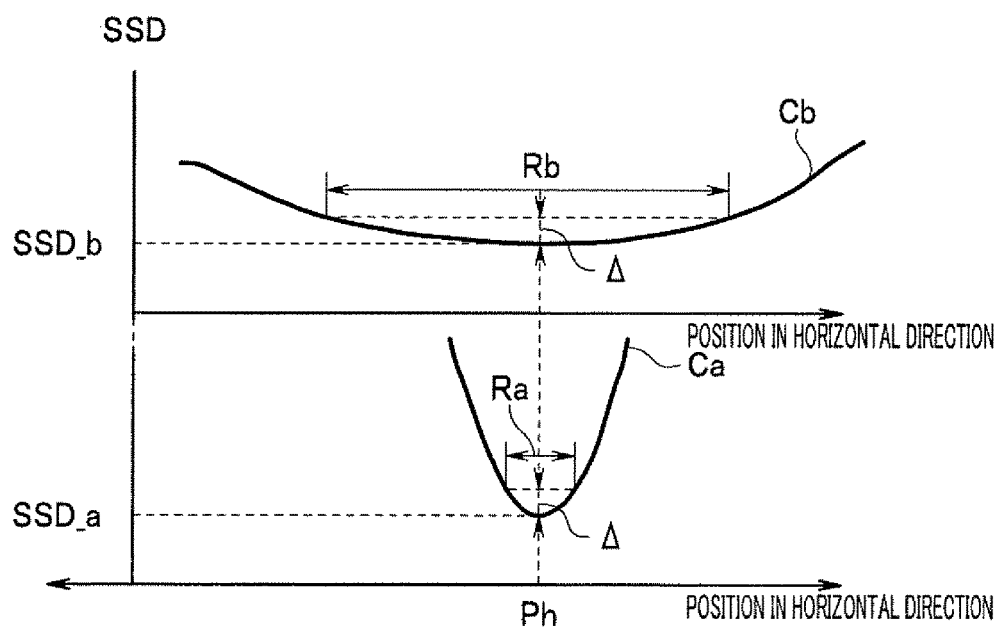
FIG. 5B is a diagram showing an example of distributions of the SSD with respect to, for example, the displacement in the horizontal direction calculated by the block matching, for example, when a blur of an image is small and when the blur is large.

On the other hand, for example, in FIG. 5B, a characteristic Cb with low reliability is shown as, for example, a characteristic with respect to a position in the horizontal direction together with the characteristic Ca.

As explained above, in the case of the characteristic Ca, the value of the SSD is the minimum value SSD_a in the position Ph in the horizontal direction and the value of the SSD greatly changes with respect to a small position change from the position Ph.

On the other hand, in the case of the characteristic Cb, the value of the SSD is a minimum value SSD_b, which is substantially the same value as the value in the case of the characteristic Ca, in the position Ph in the horizontal direction. A change in the value of the SSD is small with respect to a position change from the position Ph.

For example, when SSD_a and SSD_b include an error of approximately a value 4 due to noise or the like, in the case of the characteristic Ca, the value of the SSD is a value in a range Ra slightly deviating from the position Ph. Reliability of the position Ph is high. On the other hand, in the case of the characteristic Cb, the value of the SSD is a value in a wide range Rb from the position Ph. Reliability of the position Ph in this case is low. That is, by comparing the values of the ranges Ra and Rb with a predetermined threshold, it is possible to determine whether the reliability of the position Ph is high or low, that is, reliability of a value itself of a movement amount is high or low.

Therefore, when the discrimination of the image scene and the classification of the endoscopic procedure scene are performed using a feature value of the movement amount in the case of the characteristic Ca, the endoscopic-procedure-scene-reliability determining section 53a determines that a classification result of the endoscopic procedure scene is not low concerning the movement amount. On the other hand, when the classification of the endoscopic procedure scene is performed using a feature value of the movement amount in the case of the characteristic Cb, since the reliability of the value itself of the movement amount is low, the endoscopic-procedure-scene-reliability determining section 53a determines that reliability of the endoscopic procedure scene classified using the movement amount is low.

Figure 6A:
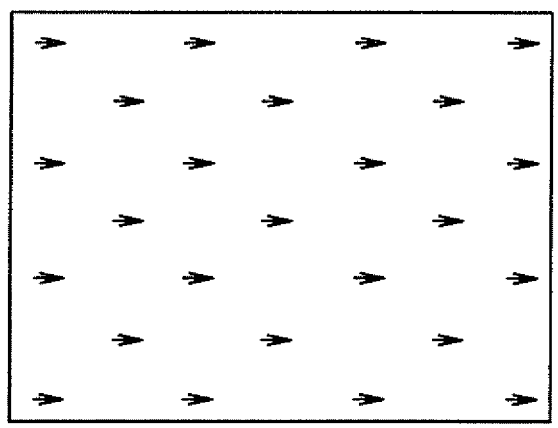
FIG. 6A is a diagram showing a representative image scene discriminated on the basis of the movement amount.
Figure 6B:
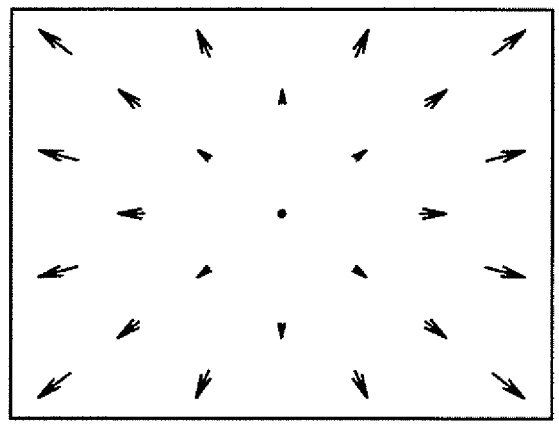
FIG. 6B is a diagram showing a representative image scene discriminated on the basis of the movement amount.
Figure 6C:
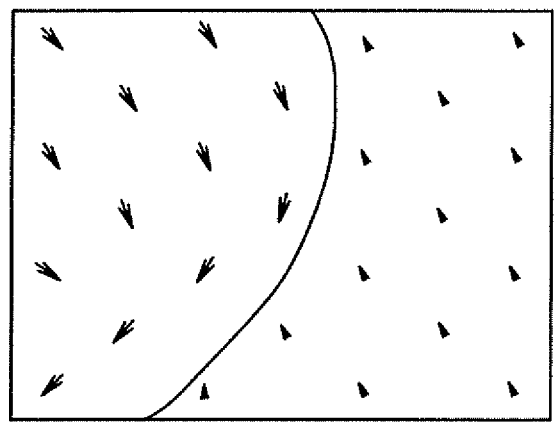
FIG. 6C is a diagram showing a representative image scene discriminated on the basis of the movement amount.
Figure 6D:
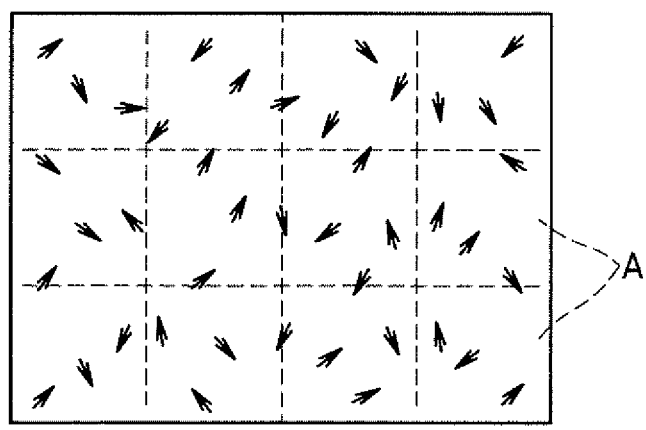
FIG. 6D is a diagram showing an exceptional image scene in which an endoscopic procedure scene cannot be classified.

FIG. 6A to FIG. 6C are diagrams showing a plurality of representative image scenes discriminated on the basis of movement amounts. FIG. 6D is a diagram showing an exceptional image scene in which an endoscopic procedure scene cannot be classified. As explained below, the image scene shown in FIG. 6D other than FIG. 6A to FIG. 6C corresponds to an endoscopic procedure scene of an unclassifiable scene.

As explained below, an image scene is discriminated as a plurality of representative image scenes and classified as an endoscopic procedure scene according to distributions of magnitudes (serving as feature values) of movement amounts in a plurality of representative positions in an image for one frame. The image scene shown in FIG. 6A indicates an image scene of translation in which movement amounts in a representative plurality of positions in an image are substantially equal (in FIG. 6A, an image scene of translation to the right side).

The image scene shown in FIG. 6B indicates an image scene of a back-and-forth movement in which a movement amount on a center side in an image is small and the movement amount radially increases (stepwise) toward a peripheral side.

The image scene shown in FIG. 6C indicates an image scene of a partial movement in which a movement exists in, for example, a left side portion in an image but a movement amount is small or almost no movement exists in a right side portion. For example, an example is assumed in which an organ close to a heart is moving in the left side portion and a hardly moving portion on the right side of the organ is observed in detail or an example is assumed in which the surgeon is performing a surgical operation while treating a part near a diseased part with a treatment instrument. Therefore, the image scene of the partial movement can also be considered an image scene partially without a movement. Such an image scene of the partial movement or an image scene partially without a movement is classified into an endoscopic procedure scene of a treatment scene in which a high-quality image is desired. FIG. 7A shows an example of an endoscopic procedure scene classified from an image scene discriminated by a movement amount and shows a relation of a set target compression ratio. As shown in FIG. 7A, the image scene of the partial movement is classified into a treatment scene. The image scene of the translation is classified into an endoscopic procedure scene of a presence diagnosis scene or a qualitative and quantitative diagnosis scene according to magnitude of a movement amount. The image scene in the back-and-forth movement is classified into an insertion scene, the presence diagnosis scene, or the qualitative and quantitative diagnosis scene according to magnitude of a movement amount.

On the other hand, the image scene shown in FIG. 6D is an unclassifiable scene that cannot be reasonably classified because a movement amount irregularly varies in a local region A (indicated by a dotted line). A distribution (arrangement) of magnitude of a movement amount in a detected image cannot be classified into the three image scenes described above. Therefore, in some case, the image scene corresponds to the unclassifiable scene.

The endoscopic-procedure-scene classifying section 53 specifies (classifies) an endoscopic procedure scene from a feature value of the distribution (including magnitude) in the image having the movement amount detected by the movement-amount detecting section 52a and sets the specified endoscopic procedure scene and a target compression ratio, for example, as shown in FIG. 7A or FIG. 7B. Characteristics of images and image scenes in this case are as shown in FIG. 7B.

As shown in FIG. 7B, the insertion scene in a scene item of the endoscopic procedure scene comes under a case in which the movement amount is large or the distance is large as the characteristic of the image. The image scene of the back-and-forth movement mainly corresponds to the insertion scene. The target compression ratio is large (high). The presence diagnosis scene comes under a case in which the movement amount is medium to large or the distance is medium to large as the characteristic of the image. The image scene of the translation or the back-and-forth movement mainly corresponds to the presence diagnosis scene. The target compression ratio is medium.

The qualitative and quantitative diagnosis scene comes under a case in which the movement amount is small (low) to medium or the distance is small to medium as the characteristic of the image. The image scene of the translation or the back-and-forth movement mainly corresponds to the qualitative and quantitative diagnosis scene. The target compression ratio is small (low). The treatment scene comes under a case in which the movement amount is small to medium or the distance is small to medium as the characteristic of the image. The image scene of the partial movement mainly corresponds to the treatment scene. The target compression ratio is small (low). In the partial movement scene, the movement and the distance are different only in a part of the image. A compression parameter defined by the target compression ratio may be used instead of the target compression ratio.

Besides the scene items of the endoscopic procedure scene normally classified as explained above, the unclassifiable scene comes under a case in which a value of the movement amount or a value of the distance fluctuates as the characteristic of the image (see FIG. 6D) or calculation accuracy is low (see FIG. 5B). The target compression ratio is decided by a preceding frame.

When the target compression ratio is decided according to the gist of FIG. 7B, the target compression ratio may be defined as large (100 KB), medium (150 KB), and small (180 KB) using, for example, a data amount after compression. Note that KB represents kilobyte. The target compression ratio may be defined as large ($\frac{1}{20}$ times), medium ($\frac{1}{15}$ times), and small ($\frac{1}{12}$ times) using, for example, a compression ratio. Even in the same endoscopic procedure scene, a value of the target compression ratio may be changed according to the movement amount and the distance.

When (the reliability of the endoscopic procedure scene is not determined as low by the endoscopic-procedure-scene-reliability determining section 53a and) the image scene is classified into one of the classification target endoscopic procedure scenes as explained above, (when a detected physical quantity is a movement amount,) the endoscopic-procedure-scene classifying section 53 sends information concerning the magnitude of the movement amount to the target-compression-ratio deciding section 54 together with a classification result. In this case, the classification of the endoscopic procedure scene is confirmed.

The target-compression-ratio deciding section 54 reads out, from the classification result of the endoscopic procedure scene and the information concerning the magnitude of the movement amount sent from the endoscopic-procedure-scene classifying section 53, from the LUT 56, a target compression ratio corresponding to the classification result of the endoscopic procedure scene and the magnitude of the movement amount and (, when the detected physical quantity is the movement amount,) decides a target compression ratio.

FIG. 7C shows content of a table of the LUT 56 prepared in advance for deciding a target compression ratio according to the endoscopic procedure scene and the movement amount. In FIG. 7C, the content of the table in the case of the movement amount is shown. However, FIG. 7D shows content of a table of the LUT 56 prepared in advance for deciding a target compression ratio according to a distance instead of the movement amount. As explained above, the endoscopic procedure scene can be classified into the insertion scene (a movement scene), the presence diagnosis scene (a screening scene), the qualitative and quantitative diagnosis scene (a close inspection scene), the treatment scene, and the unclassifiable scene. In FIG. 7C and FIG. 7D, the target compression ratio is set as explained below.

For example, in the insertion scene, when the movement amount is large, the target compression ratio is set to large in the same manner as when the distance is large. When the movement amount is medium, the target compression ratio is set to medium in the same manner as when the distance is medium. When the movement amount is small, the target compression ratio is set to small in the same manner as when the distance is small. In the case of the presence diagnosis scene, when the movement amount is large or medium, the target compression ratio is set to medium in the same manner as when the distance is large or medium. When the movement amount is small, the target compression ratio is set to small in the same manner as when the distance is small. In the qualitative and quantitative diagnosis scene, when the movement amount is medium or small, the target compression ratio is set to small in the same manner as when the distance is medium or small. In the treatment scene, the target compression ratio is set the same as in the case of the qualitative and quantitative diagnosis scene. The unclassifiable scene is calculated from the case of the preceding frame.

Note that the tables for deciding the target compression ratio shown in FIG. 7C and FIG. 7D indicate one specific example. For example, the target compression ratio may be more finely set.

In this way, the target-compression-ratio deciding section 54 decides a target compression ratio of an image to be transmitted from the classification result (and the magnitude of the movement amount) of the endoscopic procedure scene referring to the LUT 56 having the table content shown in FIG. 7C. Information concerning the target compression ratio decided by the target-compression-ratio deciding section 54 is inputted to the compression-parameter deciding section 57. The compression-parameter deciding section 57 decides a compression parameter for compression to the target compression ratio. The compression-parameter deciding section 57 sends the decided compression parameter to the wireless transmission section 34. The wireless transmission section 34 wirelessly transmits information concerning the inputted compression parameter to the wireless endoscope 2I. The wireless endoscope 2I compresses image data to be wirelessly transmitted using the transmitted compression parameter.

Note that, as the LUT 56, besides association (combination) of the endoscopic procedure scene and the target compression ratio of the table contents shown in FIG. 7C in which the movement amount is detected and FIG. 7D in which the distance is detected, for example, when both of the movement amount and the distance are detected, a table including association shown in FIG. 7E can be adopted. FIG. 7E shows content including the target compression ratio set according to the classified endoscopic procedure scene together with content in which the endoscopic procedure scene is classified from the image scene, the movement amount, and the distance.

For example, when the image scene is the translation and the movement amount is large, the insertion scene, the presence diagnosis scene, and the qualitative and quantitative diagnosis scene are classification candidates of the endoscopic procedure scene. In that case, the endoscopic procedure scene is classified into the insertion scene, the presence diagnosis scene, and the qualitative and quantitative diagnosis scene according to lager, medium, and small distances. The target compression ratio is set to large, medium, and small according to the insertion scene, the presence diagnosis scene, and the qualitative and quantitative diagnosis scene into which the endoscopic procedure scene is classified.

When the image scene is the translation and the movement amount is medium, the presence diagnosis scene and the qualitative and quantitative diagnosis scene are classification candidates of the endoscopic procedure scene. In that case, the endoscopic procedure scene is classified into the presence diagnosis scene, the qualitative and quantitative diagnosis scene, and the qualitative and quantitative diagnosis scene according to large, medium, and small distances. The target compression ratio is set to medium and small according to the presence diagnosis scene and the qualitative and quantitative diagnosis scene into which the endoscopic procedure scene is classified.

When the image scene is the translation and the movement amount is small, the presence diagnosis scene and the qualitative and quantitative diagnosis scene are classification candidates of the endoscopic procedure scene. In that case, the endoscopic procedure scene is classified into the presence diagnosis scene, the qualitative and quantitative diagnosis scene, and the qualitative and quantitative diagnosis scene according to large, medium, and small distances. The target compression ratio is set to medium and small according to the presence diagnosis scene and the qualitative and quantitative diagnosis scene into which the endoscopic procedure scene is classified.

When the image scene is the back-and-forth movement and the movement amount is large, the insertion scene and the presence diagnosis scene are classification candidates of the endoscopic procedure scene. In that case, the endoscopic procedure scene is classified into the insertion scene, the presence diagnosis scene, and the presence diagnosis scene according to large, medium, and small distances. The target compression ratio is set to large and medium according to the insertion scene and the presence diagnosis scene into which the endoscopic procedure scene is classified.

When the image scene is the back-and-forth movement and the movement amount is medium, the insertion scene, the presence diagnosis scene, and the qualitative and quantitative diagnosis scene are classification candidates of the endoscopic procedure scene. In that case, the endoscopic procedure scene is classified into the insertion scene, the presence diagnosis scene, and the qualitative and quantitative diagnosis scene according to large, medium, and small distances. The target compression ratio is set to large, medium, and small according to the insertion scene, the presence diagnosis scene, and the qualitative and qualitative diagnosis scene into which the endoscopic procedure scene is classified.

When the image scene is the back-and-forth movement and the movement amount is small, the presence diagnosis scene and the qualitative and quantitative diagnosis scene are classification candidates of the endoscopic procedure scene. In that case, the endoscopic procedure scene is classified into the presence diagnosis scene, the qualitative and quantitative diagnosis scene, and the qualitative and quantitative diagnosis scene according to large, medium, and small distances. The target compression ratio is set to medium and small according to the presence diagnosis scene and the qualitative and qualitative diagnosis scene into which the endoscopic procedure scene is classified.

When the image scene is the partial movement, the endoscopic procedure scene is classified into the treatment scene. The target compression ratio is set to small. In other image scenes, the endoscopic procedure scene is classified into the unclassifiable endoscopic procedure scene. The target compression ratio is set (decided) by an endoscopic procedure scene of an image of a preceding frame.

As modes of the association (the combination) of the endoscopic procedure scene and the target compression ratio, for example, a plurality of modes such as a standard mode for performing low compression and a power saving mode for performing high compression may be prepared to enable a user to set (select) a mode to be used. The LUT 56 is not limited to the table for deciding the target compression ratio from the classified endoscopic procedure scene and at least one of the movement amount and the distance. The LUT 56 may be a table for deciding the target compression ratio from the image scene and at least one of the movement amount and the distance. As the LUT 56, a table including table content of FIG. 7F may be adopted instead of FIG. 7E.

On the other hand, when reliability (calculation accuracy) of the value of the movement amount calculated as explained with reference to FIG. 5B is low or in the case of the exceptional scene shown in FIG. 6D, the endoscopic-procedure-scene-reliability determining section 53a determines that reliability of the unclassifiable scene serving as the endoscopic procedure scene corresponding to the exceptional scene is low.

The endoscopic-procedure-scene classifying section 53 determines that an image in which reliability of an endoscopic procedure scene is determined as low is the same as an endoscopic procedure scene of an image of an immediately preceding frame of a frame of the image. Alternatively, the endoscopic-procedure-scene classifying section 53 determines that the endoscopic procedure scene is the same as an endoscopic procedure scene of an image of a frame a plurality of frames preceding the frame of the image.

In this way, the endoscopic-procedure-scene classifying section 53 determines that the image in which the reliability of the endoscopic procedure scene is determined as low is the same as an endoscopic procedure scene of an image of a frame preceding, by a predetermined period, the frame of the image. Note that, when the endoscopic-procedure-scene classifying section 53 determines that the image in which the reliability of the endoscopic procedure scene is determined as low is the same as an endoscopic procedure scene of an image of a frame several frames preceding the frame of the image, the user such as the surgeon may be able to set information such as the number of frames or a frame period in that case from the user IF section 36. As in an operation example explained below, when a plurality of endoscopic procedure scenes classified in the past exist, for example, the endoscopic-procedure-scene classifying section 53 determines (classifies) that the endoscopic procedure scene is the same as a latest endoscopic procedure scene in the endoscopic procedure scenes classified in the past. Alternatively, the endoscopic-procedure-scene classifying section 53 estimates, according to a change of the endoscopic procedure scene, the latest endoscopic procedure scene from the plurality of endoscopic procedure scenes classified in the past. For example, when a plurality of frames in the past are classified as the presence diagnosis scene and a movement amount in that case increases little by little, the endoscopic-procedure-scene classifying section 53 determines that the endoscopic procedure scene shifts from the presence diagnosis scene to the insertion scene.

In this way, in the case of the image in which the reliability of the endoscopic procedure scene is determined as low, the endoscopic procedure scene is determined the same as an endoscopic procedure scene of an image of a frame preceding the image. A target compression ratio corresponding to the endoscopic procedure scene of the preceding frame is set (decided).

Further, classification of an endoscopic procedure scene and decision of a target compression ratio in the case in which the distance detecting section 52b is used are explained. Distances in a plurality of representative positions in one image of left and right images (signals) picked up by the left image pickup section 29a and the right image pickup section 29b and inputted to the distance detecting section 52b through the image acquiring section 51 are calculated by the distance detecting section 52b. Note that the respective positions in the image respectively correspond to respective regions in a subject, an image of which is picked up. Therefore, it may be considered that distances between a representative plurality of positions in the subject and the image pickup section 22B (or a distal end of the distal end portion 8a) are calculated.

Figure 8A:
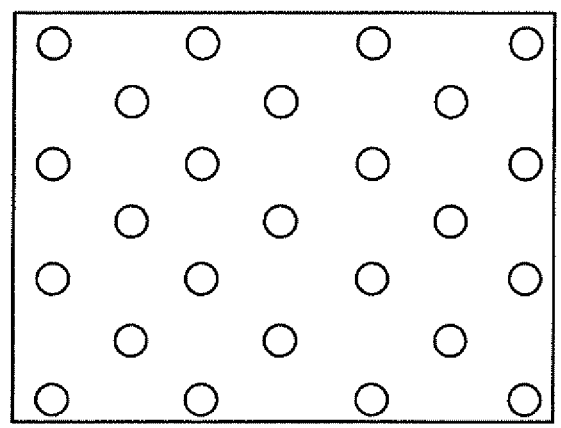
FIG. 8A is a diagram showing a representative image scene discriminated on the basis of a distance.
Figure 8B:
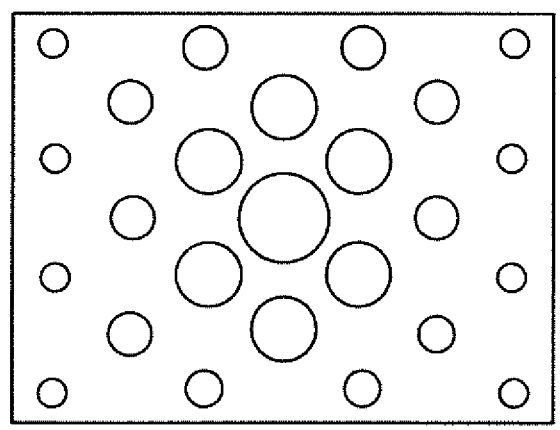
FIG. 8B is a diagram showing a representative image scene discriminated on the basis of a distance.
Figure 8C:
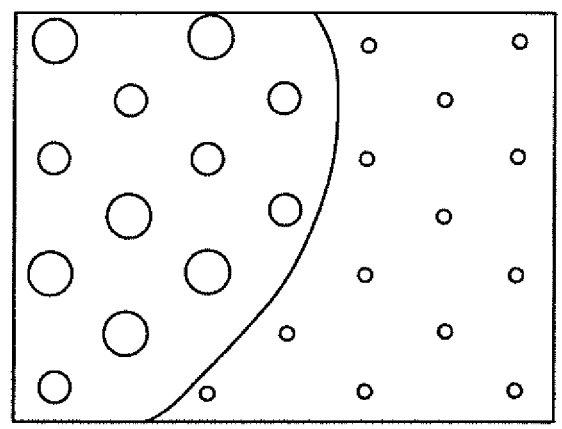
FIG. 8C is a diagram showing a representative image scene discriminated on the basis of a distance.
Figure 8D:
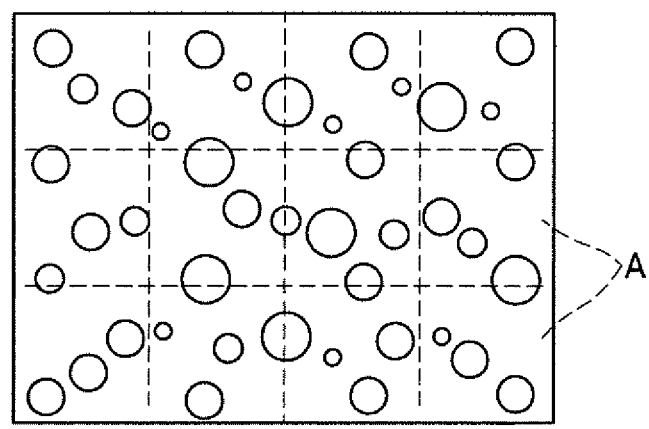
FIG. 8D is a diagram showing an exceptional scene that cannot be discriminated on the basis of a distance.

FIGS. 8A to 8C are diagrams showing distances (information) in the case of a plurality of representative image scenes discriminated on the basis of the distances. FIG. 8D is a diagram showing an exceptional image scene. The image scene shown in FIG. 8A indicates an image scene of translation in which distances in a representative plurality of positions in an image are, for example, large. Note that, in FIG. 8A to FIG. 8D, a size of a circle represents magnitude of a distance.

The image scene shown in FIG. 8B indicates an image scene of back-and-forth movement in which a distance on a center side in an image is large and the distance radially decreases toward a peripheral side.

The image scene shown in FIG. 8C indicates an image scene of partial movement in which a distance changes in, for example, a left side portion in an image but the distance does not change in a region in a right side portion. Note that, besides, as an image scene, an image scene without movement in which a distance is small in an entire image may be included in the image scene of the partial movement in the image scene shown in FIG. 8C.

On the other hand, the image scene shown in FIG. 8D is an exceptional image scene because a value of a distance irregularly varies (fluctuates) to a value equal to or larger than a threshold in a local region A (indicated by a dotted line).

The endoscopic-procedure-scene classifying section 53 discriminates the three image scenes shown in FIG. 8A to FIG. 8C from a feature value of a distribution in an image of distance (information) detected by the distance detecting section 52*b* and classifies, according to magnitude of the distance, to which endoscopic procedure scene the image scene corresponds as shown in FIG. 7B.

The endoscopic-procedure-scene classifying section 53 determines that an exceptional image scene, in which on the basis of a feature value of a distribution in the image of (a value of) the distance detected by the distance detecting section 52*b*, the distance irregularly varies in the local region A as in the image scene shown in FIG. 8D, is also an unclassifiable scene and reliability of the image scene is low.

The endoscopic-procedure-scene classifying section 53 sends information concerning the magnitude of the distance to the target-compression-ratio deciding section 54 together with information concerning the endoscopic procedure scene classified as explained above. In this case, the classification of the endoscopic procedure scene is confirmed.

The target-compression-ratio deciding section 54 reads out, from the LUT 56, a target compression ratio corresponding to a discrimination result of the endoscopic procedure scene and the information concerning the magnitude of the distance sent from the endoscopic-procedure-scene classifying section 53 and decides a target compression ratio of the image.

As explained above, FIG. 7D shows table content of the LUT 56 used in the case of distances prepared in advance.

As explained above, in the insertion scene, when the distance is large, the target compression ratio is set to large, when the distance is medium, the target compression ratio is set to medium, and, when the distance is small, the target compression ratio is set to small. In the presence diagnosis scene, when the distance is large, medium, and small, the target compression ratio is set respectively to medium, small, and small. In the qualitative and quantitative diagnosis scene and the treatment scene, when the distance is medium or small, the target compression ratio is set to small. Note that, in the case of the unclassifiable scene, the target compression rate is set to a target compression rate by an endoscopic procedure scene classified with respect to an image of a temporally preceding frame as explained in the case of the movement amount.

In this way, the target-compression-ratio deciding section 54 decides a target compression ratio of a decision target image referring to the LUT 56 including the table content shown in FIG. 7D. Information concerning the target compression ratio decided by the target-compression-ratio deciding section 54 is inputted to the compression-parameter deciding section 57. The compression-parameter deciding section 57 decides a compression parameter for compression to the target compression ratio. The compression-parameter deciding section 57 sends the decided compression parameter to the wireless transmission section 34. The wireless transmission section 34 wirelessly transmits information concerning the inputted compression parameter to the wireless endoscope 2I. The wireless endoscope 2I compresses image data to be wirelessly transmitted using the transmitted compression parameter.

On the other hand, as explained with reference to FIG. 5B, when accuracy of calculation of a distance is low or in the case of an un-separable scene (serving as an endoscopic procedure scene) corresponding to the exceptional image scene as shown in FIG. 8D, the endoscopic-procedure-scene-reliability determining section 53*a* determines that reliability of the endoscopic procedure scene is low.

As in the case of the movement amount explained above, in the case of an image in which reliability of an endoscopic procedure scene is low, the endoscopic procedure scene is determined as the same endoscopic procedure scene as an image of a frame preceding the image. A target compression ratio corresponding to the endoscopic procedure scene of the preceding frame is set (decided).

The endoscope system 1 according to the embodiment includes the wireless endoscope 2A or 2B configured to be inserted into a subject and forming an endoscope body including the image pickup section 22A or 22B provided at the distal end portion 8*a* and the wireless transmission section 24 configured to form a first wireless transmission section configured to wirelessly transmit an image signal picked up by the image pickup section 22A or 22B, the processor 3 arranged on an outside of the subject and including the wireless transmission section 34 forming a second wireless transmission section configured to receive a wirelessly-transmitted image signal and the image processing section 33 configured to perform image processing of the wirelessly-transmitted image signal, the endoscopic-procedure-scene classifying section 53 configured to form a scene classifying section configured to classify, on the basis of an image signal obtained by picking up an image of a region in the subject with the image pickup section 22A or 22B, to which endoscopic procedure scene in a plurality of representative endoscopic procedure scenes (an insertion scene, a presence diagnosis scene, a qualitative and quantitative diagnosis scene, and a treatment scene) a scene of an image for observing the region by the endoscope body corresponds, the endoscopic-procedure-scene-reliability determining section 53*a* forming a scene-reliability determining section configured to perform determination of reliability of the scene classified by the scene classifying section, and the target-compression-ratio deciding section 54 forming an image-signal-target-compression-ratio deciding section configured to, when the scene-reliability determining section determines that the reliability of the scene classified by the scene classifying section is low, decide a target compression ratio of the image signal wirelessly transmitted by the first wireless transmission section according to a classification result of an endoscopic procedure scene by the scene classifying section in an image signal of a frame preceding, by a predetermined period, a frame of the image signal, the reliability of which is determined as low.

Figure 9:
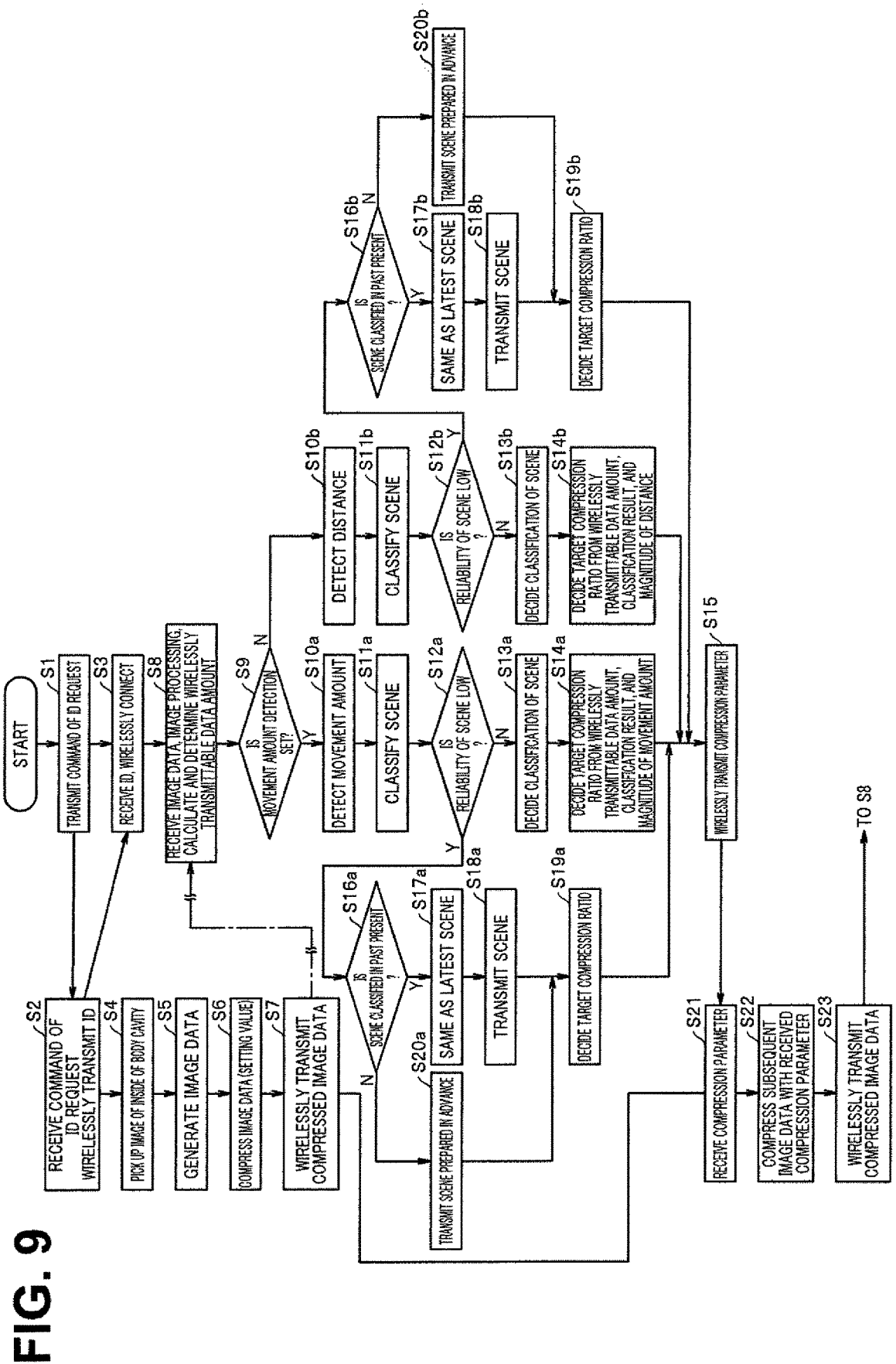
FIG. 9 is a flowchart showing processing contents of the wireless endoscope and the processor in the endoscope system according to the first embodiment.

Operation in the embodiment is explained with reference to FIG. 9. FIG. 9 shows representative processing of the wireless endoscope 2I and the processor 3 in the embodiment. Note that a flowchart portion on a leftmost side in FIG. 9 shows processing on the wireless endoscope 2I side. A right side of the flowchart portion indicates processing on the processor 3 side. Note that, on the drawing of FIG. 9, an endoscopic procedure scene is simply represented as scene.

When power supplies of the wireless endoscope 2I and the processor 3 are turned on, the wireless endoscope 2I and the processor 3 come into an operation state.

In first step S1, the control section 31 of the processor 3 wirelessly transmits, from the wireless transmission section 34, a command of an ID (transmission) request to request the wireless endoscope 2I to transmit an ID. The wireless endoscope 2I receives the command in step S2 and wirelessly transmits the requested ID. As shown in step S3, the processor 3 receives the ID and comes into a connection state in which the processor 3 wirelessly communicates with the wireless endoscope 2I. Note that, by receiving the ID, the processor 3 recognizes (identifies) whether a type of the image pickup section 22I of the wireless endoscope 2I that transmits the ID is a 22A type including one image pickup device or a 22B type including two image pickup devices.

In next step S4, the wireless endoscope 2I starts image pickup of an inside of a body cavity of a subject with the image pickup section 22I. In step S5, the image processing section 23 of the wireless endoscope 2I generates image data (before compression) of the image picked up by the image pickup section 22I. In step S6, the image processing section 23 of the wireless endoscope 2I compresses the image data with a preset compression parameter. When the image data is wirelessly transmitted (communicated), a wirelessly transmittable data amount is limited. Therefore, it is necessary to adjust a data amount to be transmitted with image compression not to be larger than the wirelessly transmittable data amount.

In step S7, the wireless transmission section 24 of the wireless endoscope 2I wirelessly transmits the compressed image data. In step S8, the wireless transmission section 34 of the processor 3 receives the compressed image data. The image processing section 33 performs image processing for resetting the compressed image data to the image data before the compression. When image data wirelessly transmitted first from the wireless transmission section 24 to the wireless transmission section 34 is received, the wirelessly-transmittable-data-amount calculating section 51a in the image processing section 33 calculates a wirelessly transmittable data amount. The wirelessly-transmittable-data-amount determining section 51b determines that the wirelessly-transmitted image data is within a range of a wirelessly transmittable data amount.

For example, when image data is transmitted first, a plurality of image data with a rate of a transmission data amount changed may be transmitted to enable the wirelessly-transmittable-data-amount determining section 51b to determine the wirelessly transmittable data amount. If the wirelessly-transmitted image data exceeds the range of the wirelessly transmittable data amount, the wirelessly-transmittable-data-amount determining section 51b increases a compression parameter of the image data, transmits a signal of a transmission request for more largely compress and transmit the image data to the wireless transmission section 24 of the wireless endoscope 2I through the wireless transmission section 34, and sets the image data wirelessly transmitted from the wireless endoscope 2I to the processor 3 within the range of the wirelessly transmittable data amount.

Figure 10:
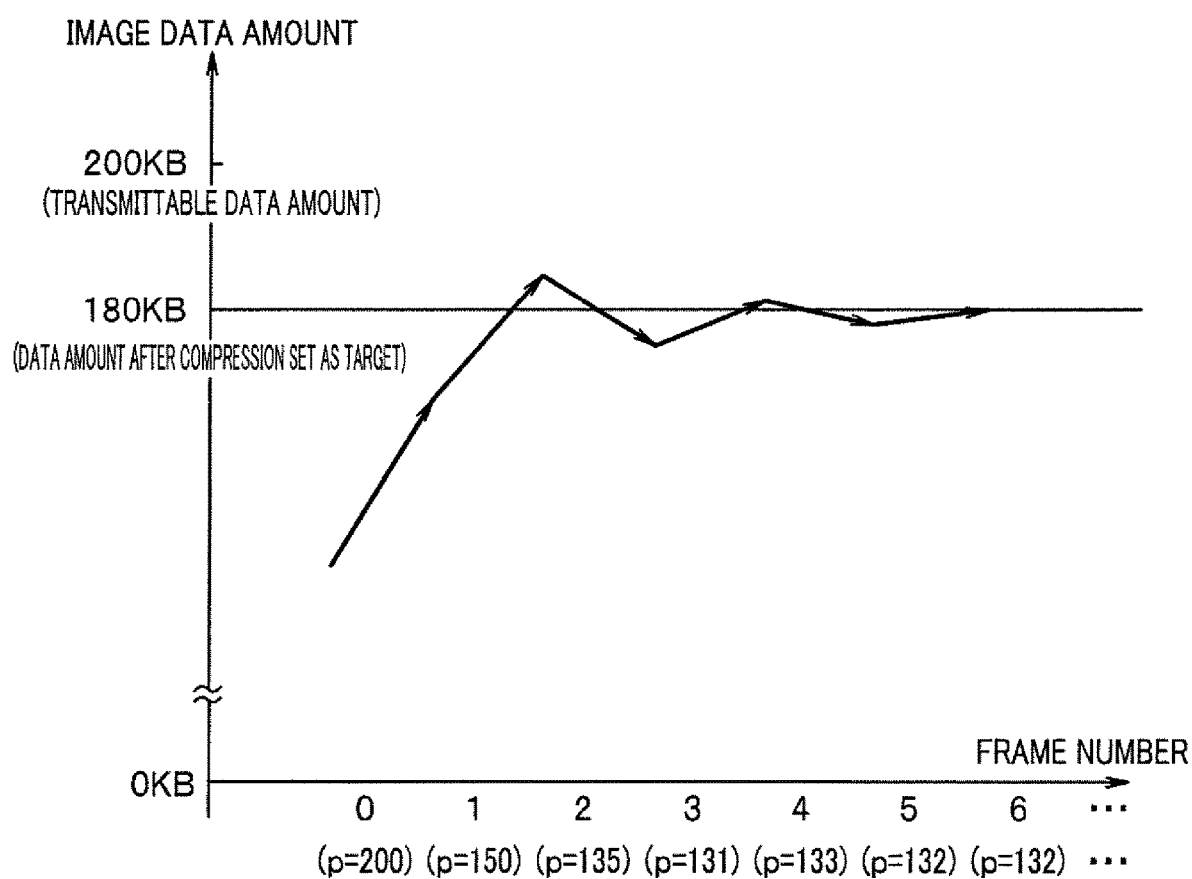
FIG. 10 is a diagram showing a state of transition of an image data amount in a control method for setting a target compression ratio to a ratio equal to or smaller than a transmittable data amount, changing a value of a compression parameter together with a frame number, and wirelessly transmitting image data.

FIG. 10 shows, as a change of a frame number, transition of an image data amount wirelessly transmitted from the wireless transmission section 24 of the wireless endoscope 2I to the wireless transmission section 34 of the processor 3 after the calculation of the wirelessly transmittable data amount by the wirelessly-transmittable-data-amount determining section 51b.

For example, whereas a picked-up image is image data of 2000 kilobyte (abbreviated as 2000 KB), if the wirelessly transmittable data amount is 200 KB, the image data has to be compressed to ¹⁄₁₀. In this case, the image processing section 23 of the wireless endoscope 2I performs image compression on the basis of a compression parameter. Note that, as the compression parameter is set to a larger value, compression is higher (larger) and, as the compression parameter is set to a smaller value, compression is lower.

When the compression parameter is represented as p, a data amount after the image compression can be changed by changing the compression parameter p. However, a final data amount is decided by the compression parameter p and an image. If the image is an image less easily compressed, the data amount after the compression is different even if compression parameter p is the same (in other words, a compression ratio is different even if the compression parameter p is the same).

Therefore, a target compression ratio has to be defined and, while the data amount after the compression is monitored together with the compression parameter p, the compression parameter p has to be updated as appropriate such that the data amount after the image compression does not exceed the wirelessly transmittable data amount.

When the wirelessly transmittable data amount is, for example, 200 KB, if the data amount exceeds 200 KB, the image cannot be transmitted. Therefore, a target data amount after the compression is set to, for example, 180 KB, which is a value 10% smaller than 200 KB.

In the example shown in FIG. 10, a control method for setting an initial value of the compression parameter p to a large value of 200, setting a data amount after image compression sufficiently small first, and bringing the data amount close to a target compression ratio is adopted. By adopting the control method shown in FIG. 10, deviation of a data amount in an image having a large frame number from the target data amount after the compression is suppressed in a small range such that wireless transmission of an image can be stably performed.

As shown in FIG. 10, a first image with a frame number 0 is compressed with the compression parameter p having a large value and transmitted. In a next frame number 1, the target compression ratio is updated according to the compressed data amount with the preceding frame number 0.

More specifically, a method of calculating a value of the compression parameter p with the frame number 1 is explained.

As explained below, first, starting from the compression parameter p with the initial value 200, the compression parameter p is calculated from the frame number 1.

| | |
|---|---|
| An input image size | 2000 KB |
| A target data amount after compression | 180 KB |
| A target compression ratio | 180 KB/2000 KB |
| The compression parameter p of the preceding frame (0) | 200 |
| A data amount of the preceding frame (0) | 40 KB |

A value of the compression parameter p of a next frame is calculated by the following function equation.

A value of the compression parameter p of the next frame=a value of the compression parameter p of the preceding frame+constant×(the data amount of the preceding frame−the target data amount after the compression)/the target data amount after the compression=200+65×(40 KB−180 KB)/180 KB=150

As the function equation for calculating a value of the compression parameter p of the next frame, various expressions are conceivable according to restrictions of the control method. As the restrictions in this case, for example, a restriction for early convergence to the target compression ratio and a restriction for a reduction of a change in quality during control are considered.

In step S9 following step S8 in FIG. 9, the control section 31 of the processor 3 determines whether a physical quantity detected by the physical-quantity detecting section 52 for deciding a target compression ratio is a movement amount. When it is recognized in step S3 that the type of the image pickup section 22I of the wireless endoscope 2I is the 22A type, in the determination processing in step S9, the control section 31 determines that the physical quantity is the movement amount.

On the other hand, when it is recognized that the type of the image pickup section of the wireless endoscope 2I is the 22B type, the surgeon selects one of the movement amount and the distance from the user IF section 36. Note that the surgeon is not limited to perform input for selecting one of the movement amount and the distance in step S9. The surgeon may perform the input for selecting one of the movement amount and the distance at a stage before step S9. As explained below, the surgeon can also perform selection for performing processing for deciding a compression ratio using both of the movement amount and the distance.

When it is selected or determined to detect the movement amount in the determination processing in step S9, in next step S10a, the movement-amount detecting section 52a detects a movement amount in a present image using an image inputted to the movement-amount detecting section 52a (referred to as present image or image of a present frame as well) and an image of an immediately preceding frame (in an image for first one frame, since an image of an immediately preceding frame is absent, does not perform the processing and starts the processing in an image of a next frame).

In next step S11a, the endoscopic-procedure-scene classifying section 53 discriminates, from a distribution in the image of the movement amount detected by the movement-amount detecting section 52a, to which representative image scene shown in FIG. 6A to FIG. 6D the image corresponds. Further, the endoscopic-procedure-scene classifying section 53 performs processing of classification of an endoscopic procedure scene shown in FIG. 7A from the image scene and magnitude of the movement amount.

In next step S12a, the endoscopic-procedure-scene-reliability determining section 53a determines whether reliability of the endoscopic procedure scene classified by the endoscopic-procedure-scene classifying section 53 is low. As explained above, when reliability of the movement amount used for the classification of the endoscopic procedure scene is low (in the case of the characteristic Cb shown in FIG. 5B) or in the case of the exceptional image scene shown in FIG. 6A to FIG. 6D, the endoscopic-procedure-scene-reliability determining section 53a determines that reliability of the (classified) endoscopic procedure scene is low. In other cases, the endoscopic-procedure-scene-reliability determining section 53a determines that the reliability of the endoscopic procedure scene is not low.

Therefore, when it is determined in the determination processing in step S12a that the reliability of the endoscopic procedure scene is not low, in next step S13a, a classification of the endoscopic procedure scene with respect to the present image classified by the endoscopic-procedure-scene classifying section 53 is decided. The endoscopic-procedure-scene classifying section 53 sends a result of the decided classification and magnitude of the movement amount at that time to the target-compression-ratio deciding section 54.

In next step S14a, the target-compression-ratio deciding section 54 reads out, using information concerning the calculated wirelessly transmittable data amount, the endoscopic procedure scene decided by the endoscopic-procedure-scene classifying section 53, and the magnitude of the movement amount, a target compression ratio corresponding to the transmittable data amount, the endoscopic procedure scene, and the magnitude of the movement amount, for example, from the LUT 56 including the content of FIG. 7C and decides a target compression ratio. The target-compression-ratio deciding section 54 decides a target compression ratio to be equal to or smaller than the calculated wirelessly transmittable data amount. When an image signal is wirelessly transmitted by the control method explained with reference to FIG. 9B, a target compression ratio of the image signal is set to be equal to or smaller than the wirelessly transmittable data amount to enable the image signal to be surely wirelessly transmitted. The decided target compression ratio is inputted to the compression-parameter deciding section 57. The compression-parameter deciding section 57 decides a compression parameter for compression to the target compression ratio and sends the compression parameter to the wireless transmission section 34.

In next step S15, the wireless transmission section 34 wirelessly transmits the decided compression parameter to the wireless endoscope 2I.

On the other hand, when it is determined in step S12a that the reliability of the endoscopic procedure scene is low, in step S16a, the endoscopic-procedure-scene classifying section 53 determines whether an endoscopic procedure scene classified in the past is present. When an endoscopic procedure scene classified in the past is present, in step S17a, the endoscopic-procedure-scene classifying section 53 determines (classifies) that, for example, the endoscopic procedure scene classified in the past is the same as a latest endoscopic procedure scene. Alternatively, the endoscopic-procedure-scene classifying section 53 estimates, according to a change of the endoscopic procedure scene, a latest endoscopic procedure scene from a plurality of endoscopic procedure scenes classified in the past. In step S18a, the endoscopic-procedure-scene classifying section 53 sends information concerning the endoscopic procedure scene to the target-compression-ratio deciding section 54 (together with magnitude of a movement amount when reliability of the movement amount is not low).

In next step S19a, the target-compression-ratio deciding section 54 reads out, using the information concerning the endoscopic procedure scene sent from the endoscopic-procedure-scene classifying section 53 or the magnitude of the movement amount at the time when the reliability of the movement amount is not low sent together with the endoscopic procedure scene from the endoscopic-procedure-scene classifying section 53, from the LUT 56, a target compression ratio corresponding to the endoscopic procedure scene or the endoscopic procedure scene and the magnitude of the movement amount and decides the target compression ratio. Thereafter, the target-compression-ratio deciding section 54 shifts to the processing in step S15. Note that, when the reliability of the movement amount is low (in other words, when a target compression ratio is decided from the information concerning only the endoscopic procedure scene), the target-compression-ratio deciding section

54 may set that the target compression ratio is decided as, for example, a largest target compression ratio in the endoscopic procedure scene.

On the other hand, when an endoscopic procedure scene classified in the past is absent in the determination processing in step S16a, as shown in step S20a, the endoscopic-procedure-scene classifying section 53 sends, to the target-compression-ratio deciding section 54, information concerning a predetermined endoscopic procedure scene prepared or set in advance, for example, information indicating that an endoscopic procedure scene does not change. In step S19a, the target-compression-ratio deciding section 54 reads out, using the information concerning the predetermined endoscopic procedure scene sent from the endoscopic-procedure-scene classifying section 53, from the LUT 56, a target compression ratio corresponding to the predetermined endoscopic procedure scene and decides the target compression ratio. In the case of FIG. 7C, in the insertion scene and the presence diagnosis scene, the target compression ratio changes according to the magnitude of the movement amount in the endoscopic procedure scene. In the qualitative and quantitative diagnosis scene and the treatment scene, the movement amount is equal to or smaller than medium. The target compression ratio is set to small.

On the other hand, when the detection of the distance is selected or determined rather than the movement amount in the determination processing in step S9, in step S10b, the distance detecting section 52b detects, from left and right images based on the left and right image pickup sections 29a and 29b having a parallax, distances in a plurality of positions in one image.

Steps S11b to S20b explained below are processing similar to steps S11a to S20a (processing in which the movement amount is replaced with the distance).

In next step S11b, the endoscopic-procedure-scene classifying section 53 discriminates, from a distribution in an image of the distances detected by the distance detecting section 52b, to which representative image scene shown in FIG. 8A to FIG. 8D the image corresponds and further performs the processing of the classification of the endoscopic procedure scene shown in FIG. 7B from a distance and magnitude of the image scene.

In next step S12b, the endoscopic-procedure-scene-reliability determining section 53a determines whether reliability of the endoscopic procedure scene classified by the endoscopic-procedure-scene classifying section 53 is low. As explained above, when reliability of the distance used in the classification of the endoscopic procedure scene is low or in the case of the exceptional scene shown in FIG. 8D (when a value of the distance irregularly varies to a value equal to or larger than a threshold in the local region A), the endoscopic-procedure-reliability determining section 53a determines that the reliability of the endoscopic procedure scene is low. In other cases, the endoscopic-procedure-reliability determining section 53a determines that the reliability of the endoscopic procedure scene is not low.

Therefore, when it is determined in the determination processing in step S12b that the reliability of the endoscopic procedure scene is not low, in next step S13b, an endoscopic procedure scene classification for a present image classified by the endoscopic-procedure-scene classifying section 53 is decided. The endoscopic-procedure-scene classifying section 53 sends a result of the decided classification and magnitude of the distance at that time to the target-compression-ratio deciding section 54.

In next step S14b, the target-compression-ratio deciding section 54 reads out, using information concerning the calculated wirelessly transmittable data amount, the endoscopic procedure scene decided by the endoscopic-procedure-scene classifying section 53, and the magnitude of the distance, from the LUT 56 shown in FIG. 7D, a target compression ratio corresponding to the calculated wirelessly transmittable data amount, the endoscopic procedure scene, and the magnitude of the distance and decides the target compression ratio. The target-compression-ratio deciding section 54 decides a target compression ratio to be equal to or smaller than the calculated wirelessly transmittable data amount. When an image signal in the case of a low target compression ratio is wirelessly transmitted, the target-compression-ratio deciding section 54 sets a target compression ratio of the image signal to be equal to or smaller than the wirelessly transmittable data amount to enable the image signal to be surely wirelessly transmitted. The decided target compression ratio is inputted to the compression-parameter deciding section 57. The compression-parameter deciding section 57 decides a compression parameter for compression to the target compression ratio and sends the compression parameter to the wireless transmission section 34.

In next step S15, the wireless transmission section 34 wirelessly transmits the decided compression parameter to the wireless endoscope 2I.

On the other hand, when it is determined in step S12b that the reliability of the endoscopic procedure scene is low, in step S16b, the endoscopic-procedure-scene classifying section 53 determines whether an endoscopic procedure scene classified in the past is present. When an endoscopic procedure scene classified in the past is present, in step S17b, the endoscopic-procedure-scene classifying section 53 determines (classifies) that, for example, the endoscopic procedure scene classified in the past is the same as a latest endoscopic procedure scene. Alternatively, the endoscopic-procedure-scene classifying section 53 estimates, according to a change of the endoscopic procedure scene, a latest endoscopic procedure scene from a plurality of endoscopic procedure scenes classified in the past. In step S18b, the endoscopic-procedure-scene classifying section 53 sends information concerning the endoscopic procedure scene to the target-compression-ratio deciding section 54 (together with magnitude of distance when reliability of the distance is not low).

In next step S19b, the target-compression-ratio deciding section 54 reads out, using information concerning the endoscopic procedure scene sent from the endoscopic-procedure-scene classifying section 53 or the magnitude of the distance at the time when the reliability of the distance is not low sent together with the endoscopic procedure scene from the endoscopic-procedure-scene classifying section 53, from the LUT 56, a target compression ratio corresponding to the endoscopic procedure scene or the magnitude of the distance and decides the target compression ratio. Thereafter, the compression-parameter deciding section 57 decides a compression parameter for compression to the target compression ratio, sends the compression parameter to the wireless transmission section 34, and shifts to the processing in step S15. Note that, when the reliability of the distance is low (in other words, when a target compression ratio is decided from the information concerning only the endoscopic procedure scene), the target-compression-ratio deciding section 54 may decide the target compression ratio as, for example, a largest target compression ratio in the endoscopic procedure scene.

On the other hand, when an endoscopic procedure scene classified in the past is absent in the determination processing in step S16b, as shown in step S20b, the endoscopicprocedure-scene classifying section 53 sends, to the target-compression-ratio deciding section 54, information concerning a predetermined endoscopic procedure scene prepared or set in advance, for example, information indicating that an endoscopic procedure scene does not change. In step S19b, the target-compression-ratio deciding section 54 reads out, using the information concerning the predetermined endoscopic procedure scene sent from the endoscopic-procedure-scene classifying section 53, from the LUT 56, a target compression ratio corresponding to the predetermined endoscopic procedure scene and decides the target compression ratio. In that case, when the target compression ratio changes according to magnitude of the distance in the endoscopic procedure scene, for example, the target compression ratio may be set to, for example, a largest target compression ratio.

As explained above, in step S15, the wireless transmission section 34 of the processor 3 wirelessly transmits information concerning a compression parameter corresponding to the decided target compression ratio to the wireless endoscope 2I.

As shown in step S21, the wireless endoscope 2I receives the information concerning the compression parameter. As shown in next step S22, the wireless endoscope 2I compresses image data wirelessly transmitted from the wireless endoscope 2I to the processor 3 using the received information concerning the compression parameter. In a next step S23, the wireless transmission section 24 of the wireless endoscope 2I wirelessly transmits the compressed image data to the processor 3. Operation after the step is the same operation as the operation in step S8 and subsequent steps. Note that the processing for wirelessly transmitting the compression parameter in step S15 and the processing for receiving the compression parameter in step S21 (and S22) do not need to be substantially synchronized. For example, when the compression parameter is wirelessly transmitted from the processor 3, the wireless transmission section 24 of the wireless endoscope 2I may temporarily save the transmitted compression parameter in a memory. That is, in step S21, processing for saving the transmitted compression parameter and compressing the image data using the transmitted compression parameter at timing different from timing when the compression parameter is transmitted may be performed.

The classification of the endoscopic procedure scene sometimes takes time. Therefore, after an end of the classification of the endoscopic procedure scene is confirmed, a next frame image may be inputted to the endoscopic-procedure-scene classifying section 53. In this way, the operation of the image pickup and the operation of the endoscopic procedure scene classification or the like may be asynchronized. The endoscopic procedure scene gradually changes in a plurality of frames rather than changing in one frame. Therefore, as explained above, the operation of the image pickup and the operation of the endoscopic procedure scene classification or the like may be asynchronized.

Note that, after the processing in step S7, the wireless endoscope 2I performs image pickup for one to several frames until the wireless endoscope 2I acquires the information concerning the compression parameter wirelessly transmitted from the processor 3 in step S21.

For example, when the processor 3 can decide a target compression ratio and the wireless endoscope 2I can acquire information concerning a compression parameter from the processor 3 in one frame period or less, the wireless endoscope 2I sequentially compresses picked-up image data using a compression parameter ratio based on image data temporally shifting by only the one frame period and wirelessly transmits the image data to the processor 3.

On the other hand, when the wireless endoscope 2I can acquire information concerning the target compression ratio in a period exceeding the one frame period, the processor 3 may perform processing for deciding a target compression ratio for each of images of a plurality of frames without performing processing for deciding (calculating) a target compression ratio for each of respective frames.

Note that, when classification of an endoscopic procedure scene can be performed within one frame period and a movement amount or a distance in an endoscopic procedure scene of a present image is detected, the movement amount or the distance in the endoscopic procedure scene of the present image may be estimated from tendencies of changes in movement amounts or magnitudes of distances in a plurality of endoscopic procedure scenes in the past. For example, when both images two frame periods and one frame period preceding the present image are classified as the same endoscopic procedure scene and, for example, movement amounts of the images the two frame periods and one frame period preceding the present image change to large and medium, an endoscopic procedure scene of a present image may be estimated as the same endoscopic procedure scene as the images and a movement amount of the endoscopic procedure scene may be estimated as small. In this case, when, for example, the movement amounts of the images the two frame periods and one frame period preceding the present image change to small and medium, an endoscopic procedure scene of a present image may be estimated as the same endoscopic procedure scene as the images and a movement amount of the endoscopic procedure scene may be estimated as large.

With the endoscope system 1 according to the embodiment operating in this way, it is possible to set an appropriate target compression ratio and wirelessly transmit an image signal even when reliability in classifying an endoscopic procedure scene with respect to an image is low. When a transmission state of the wireless transmission is grasped, a wirelessly transmittable data amount is calculated, and an image signal in the case of a low target compression ratio is wirelessly transmitted, it is possible to set a target compression ratio of the image signal to be equal to or smaller than the wirelessly transmittable data amount and surely wirelessly transmit the image signal.

When an image of an inside of a body cavity is picked up at a constant frame period (e.g., 1/30 S or 1/60 S), in one to several frame periods, an endoscopic procedure scene of the image hardly changes to an endoscopic procedure scene suddenly greatly changing from an immediately preceding endoscopic procedure scene. In most cases, the endoscopic procedure scene shows a gradually changing tendency. Therefore, it is appropriate to determine (or identify) that an endoscopic procedure scene that cannot be classified in a state in which the endoscopic procedure scene has reliability is the same as an endoscopic procedure scene that can be classified near a time immediately preceding the endoscopic procedure scene that cannot be classified. Compression with a compression parameter corresponding to a target compression ratio of the endoscopic procedure scene in that case can be evaluated as appropriate procedure.

According to the embodiment, in the case of the wireless endoscope 2B actually in use, a physical quantity used in the classification of the endoscopic procedure scene and the decision of the target compression ratio can be selected from a plurality of physical quantities. On the other hand, in the case of the wireless endoscope 2A, a physical quantity used in the classification of the endoscopic procedure scene and the decision of the target compression ratio can be automatically decided. Operability for the user such as the surgeon can be improved.

Note that, in the above explanation of the embodiment, the classification of the endoscopic procedure scene and the decision of the target compression ratio are performed using only one of the movement amount or the distance. However, the classification of the endoscopic procedure scene and the decision of the target compression ratio may be performed using information concerning both the kinds (two) information.

Figure 11:
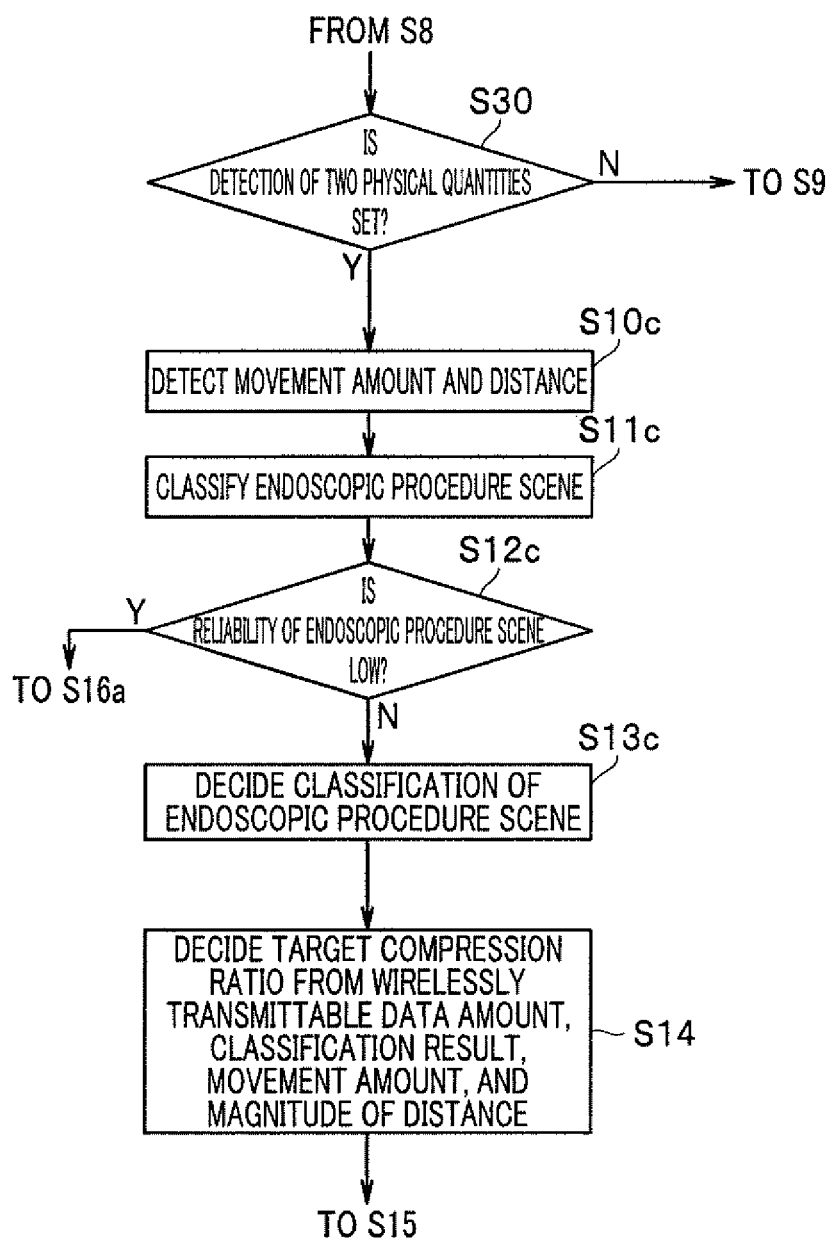
FIG. 11 is a flowchart showing a part of processing for classifying an endoscopic procedure scene according to detection of a movement amount and a distance and further deciding a target compression ratio.

Processing in the case is shown in FIG. 11. The processing shown in FIG. 11 is only partially different from the processing shown in FIG. 9. Therefore, only the differences are explained. Steps S1 to S8 are the same processing as the processing shown in FIG. 9. In step S30 following step S8, (the control section 31 of) the processor 3 determines whether setting for performing detection of two physical quantities is made. When the surgeon desires to detect a movement amount and a distance and perform classification of an endoscopic procedure scene and decision of a target compression ratio, the user performs selection of the movement amount and the distance from the user IF section 36.

Note that, when one of the movement amount and the distance is selected in the determination processing in step S30, the processing shifts to the processing in step S9 in FIG. 9. In this case, the same processing as the processing in FIG. 9 is performed.

When both of the movement amount and the distance are selected in the determination processing in step S30, as shown in FIG. 11, steps S10c to 5Bc and step S14 are performed. More specifically, in step S10c, the movement-amount detecting section 52a and the distance detecting section 52b respectively detect a movement amount and a distance. In next step S11c, the endoscopic-procedure-scene classifying section 53 classifies an endoscopic procedure scene from the movement amount and the distance. The classification of the endoscopic procedure scene may be performed from characteristics of images and image scenes as shown in FIG. 7B or may be performed from the table data shown in FIG. 7E.

When the processing of the classification of the endoscopic procedure scene is performed, as shown in step S12c, the endoscopic-procedure-scene-reliability determining section 53a determines reliability of the endoscopic procedure scene to be classified. When determining that the reliability of the endoscopic procedure scene is low, the endoscopic-procedure-scene-reliability determining section 53a shifts to, for example, processing in step S16a (or step S16b). When determining that the reliability of the endoscopic procedure scene is not low, the endoscopic-procedure-scene-reliability determining section 53a proceeds to next step S13c. In step S13c, the classification of the endoscopic procedure scene by the endoscopic-procedure-scene classifying section 53 is decided.

From a result of step S13c, in step S14, the target-compression-ratio deciding section 54 decides a target compression ratio using information concerning the calculated wirelessly transmittable data amount, a classification result of the endoscopic procedure scene, and magnitude of the movement amount and magnitude of the distance. The compression-parameter deciding section 57 decides a compression parameter from the decided target compression ratio and shifts to processing in next step S15. Note that an LUT in deciding a target compression ratio from the endoscopic procedure scene is not limited to the LUT including the table data shown in FIG. 7E. Table data shown in FIG. 7F may be used. Partially different table data such as FIG. 7E and FIG. 7F can be selected and used according to preference or the like of the user.

More specifically, in the case of the insertion scene serving as the endoscopic procedure scene, when the movement amount is large and the distance is large, medium, and small, the target compression ratio is respectively set to large, large, and medium. When the movement amount is medium and the distance is large, medium, and small, the target compression ratio is set to medium. When the movement amount is small and the distance is large, medium, and small, the target compression ratio is set to medium, small, and small.

In the case of the presence diagnosis scene, when the movement amount is large and the distance is large, medium, and small, the target compression ratio is respectively set to medium, medium, and small. When the movement amount is medium and the distance is large, medium, and small, the target compression ratio is set to small. When the movement amount is small, even when the distance is large, medium, and small, the target compression ratio is set to small.

In the case of the qualitative and quantitative diagnosis scene, the movement amount is medium or small. In the movement amounts, the target compression ratio is set to small irrespective of whether the distance is medium or small. In the case of the treatment scene, the target compression ratio is set to small as in the case of the qualitative and quantitative diagnosis scene.

When the classification of the endoscopic procedure scene and the decision of at target compression ratio are performed using the information concerning both of the movement amount and the distance in this way, the classification of the endoscopic procedure scene can be more accurately performed. A target compression ratio suitable for the classified endoscopic procedure scene can be decided. Note that the endoscopic procedure scene may be classified from a feature value of one physical quantity. The endoscopic procedure scene may be classified from a feature value of the other physical quantity. In this case, when the classified endoscopic procedure scenes or the target compression ratios are different, preferential one of the physical quantities may be decided in advance. The endoscopic procedure scene or the target compression ratio based on the preferential physical quantity may be prioritized.

Figure 12:
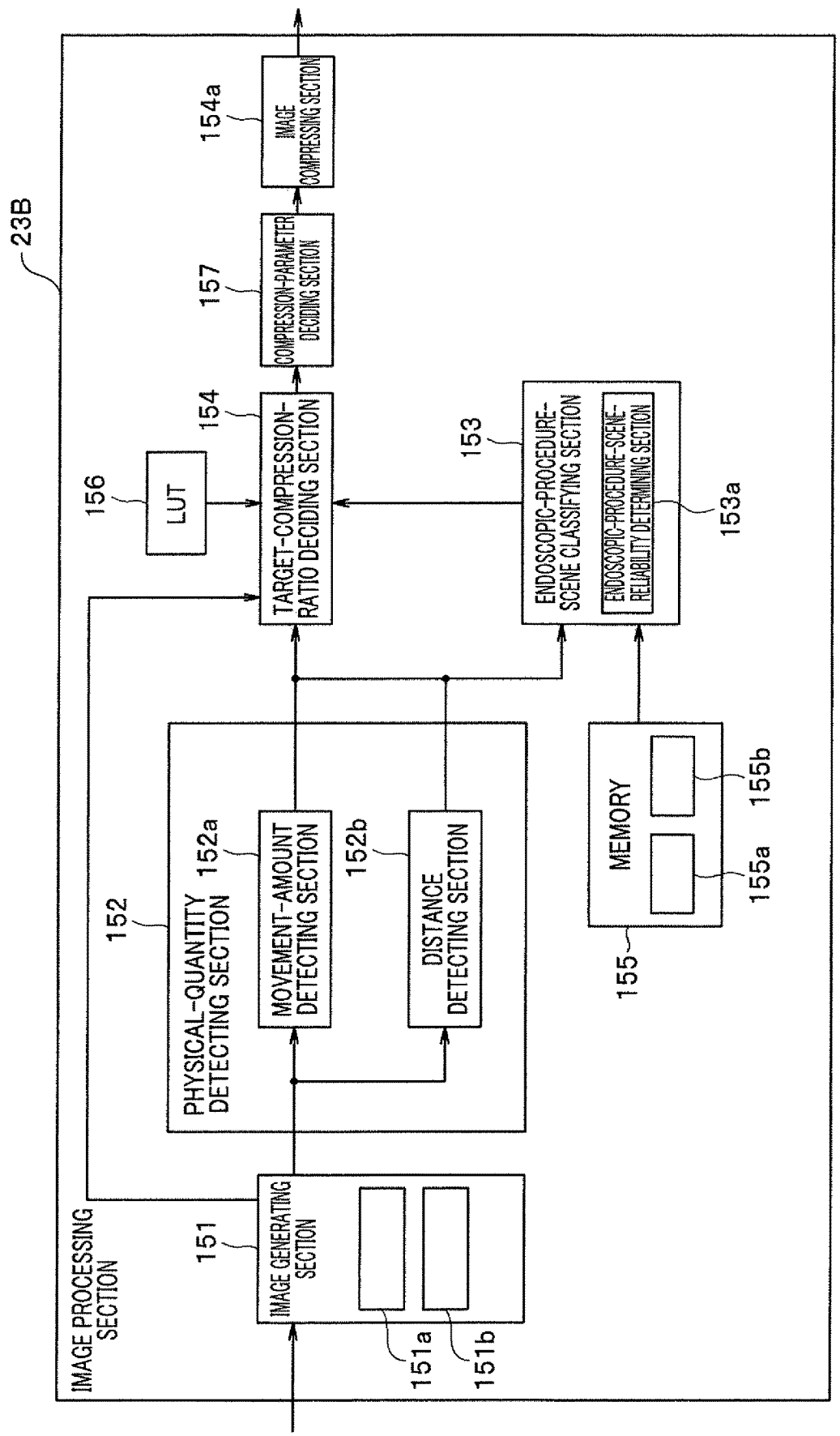
FIG. 12 is a block diagram showing a configuration of an image processing section of a wireless endoscope in an endoscope system according to a modification of the first embodiment.

In the embodiment explained above, the classification of the endoscopic procedure scene and the decision (the calculation) of the target compression ratio are performed on the processor 3 side. However, the classification of the endoscopic procedure scene and the decision (the calculation) of the target compression ratio may be performed on the wireless endoscope 2I side. FIG. 12 shows a configuration of an image processing section 23B in the case in which the classification of the endoscopic procedure scene and the decision (the calculation) of the target compression ratio are performed on the wireless endoscope 2I side in a modification of the first embodiment.

In the modification, the image processing section 23 in the wireless endoscope 2I shown in FIG. 2 is replaced with the image processing section 23B shown in FIG. 12.

The image processing section 23B shown in FIG. 12 has substantially the same configuration as the image processing section 33 shown in FIG. 3. Note that, in the modification, a target compression ratio and a compression parameter are decided on the wireless endoscope 2I side. Therefore, the image processing section 33 of the processor 3 in the case of the modification includes only the image acquiring section 51 shown in FIG. 3.

A main part of the image processing section 23B is configured by an image generating section 151 configured to generate an image signal from a picked-up image (signal) of the image pickup section 22I, a physical-quantity detecting section 152 configured to detect, on the basis of the image signal generated by the image generating section 151, a physical quantity reflecting a state in which a region in a body cavity is observed by the image pickup section 22I provided at the distal end portion 8a of the insertion section 8 in the wireless endoscope 2I, an endoscopic-procedure-scene classifying section 153 configured to classify, on the basis of a feature value of the physical quantity detected in the physical-quantity detecting section 152, to which representative endoscopic procedure scene of a plurality of representative endoscopic procedure scenes (or observation scenes) prepared or registered in advance a scene of an image in which the surgeon is performing a procedure using the wireless endoscope 2I corresponds, a target-compression-ratio deciding section 154 configured to decide, from the endoscopic procedure scene classified in the endoscopic-procedure-scene classifying section 153 and the feature value of the physical quantity (more specifically, magnitude of the physical quantity, a distribution of the physical quantity in a plurality of positions, etc.) acquired in the physical-quantity detecting section 152, a target compression ratio in wirelessly transmitting an image from the wireless endoscope 2I, a compression-parameter deciding section 157 configured to decide a compression parameter from the determined target compression ratio, and an image compressing section 154a configured to perform compression of the image signal with the compression parameter.

The image generating section 151 includes a wirelessly-transmittable-data-amount calculating section 151a configured to grasp a state of wireless transmission and calculate a wirelessly transmittable data amount and a wirelessly-transmittable-data-amount determining section 151b configured to determine the wirelessly transmittable data amount.

The wirelessly transmittable data amount calculated by the wirelessly-transmittable-data-amount calculating section 151a and a result of the determination by the wirelessly-transmittable-data-amount determining section 151b are sent to the target-compression-ratio deciding section 154. The target-compression-ratio deciding section 154 prioritizes the wirelessly transmittable data amount and the determination result to decide a target compression ratio in wirelessly transmitting the image signal. The compression-parameter deciding section 157 decides, from the decided target compression ratio, a compression parameter for compression to the target compression ratio. As explained below, the compression-parameter deciding section 157 calculates and determines a wirelessly transmittable data amount. When an image signal in the case of a low target compression ratio is wirelessly transmitted, the compression-parameter deciding section 157 sets a target compression ratio of the image signal to be equal to or smaller than the wirelessly transmittable data amount to enable the wireless transmission to be surely performed.

The physical-quantity detecting section 152 in the modification includes a movement-amount detecting section 152a configured to detect, on the basis of an image signal obtained by picking up an image of an inside of a subject with the image pickup section 22I, movement amounts in a plurality of representative regions in an image for one frame as the physical quantity and a distance detecting section 152b configured to detect, for example, a plurality of distances between a plurality of positions in the subject, an image of which is picked up by the image pickup section 22B, and the image pickup section 22B as the physical quantity.

As explained in the first embodiment, when the wireless endoscope 2B including the image pickup section 22B capable of giving stereoscopic vision is used, for example, it is possible to select, for example, from the user IF section 36, one of the movement amount detected by the movement-amount detecting section 152a and the distance detected by the distance detecting section 152b as the physical quantity detected in the physical-quantity detecting section 152 and perform classification of a scene. As explained with reference to FIG. 11, it is also possible to select the two (both) physical quantities to perform the classification of the endoscopic procedure scene and the decision of the target compression ratio.

On the other hand, when the wireless endoscope 2B including the image pickup section 22A configured by one image pickup device is used, the movement amount detected by the movement-amount detecting section 152a is selected as the physical quantity detected in the physical-quantity detecting section 152 to perform the classification of the endoscopic procedure scene.

In the wireless endoscope (2C) explained above, in a wireless endoscope including the image pickup section 22A configured of one image pickup device, it is possible to select one or both of the movement amount detected by the movement-amount detecting section 152a and the distance detected by the distance detecting section 152b and perform classification of an endoscopic procedure scene. In the following explanation, for simplification, as a wireless endoscope, the wireless endoscopes 2A and 2B are explained. However, the wireless endoscope can also be applied to the wireless endoscope 2C.

The endoscopic-procedure-scene classifying section 153 further has, besides performing the classification of the endoscopic procedure scene on the basis of the feature value of the physical quantity detected by the physical-quantity detecting section 152 as explained above, a function of an endoscopic-procedure-scene-reliability determining section 153a configured to perform determination of reliability of the classified endoscopic procedure scene.

The image processing section 23B includes a memory 155 including a representative-endoscopic-procedure-scene-feature-value storing section 155a having stored feature values representing a representative plurality of endoscopic procedure scenes at the time when the endoscopic-procedure-scene classifying section 153 performs the classification of the endoscopic procedure scene. The endoscopic-procedure-scene classifying section 153 performs the classification of the endoscopic procedure scene referring to information of the representative-endoscopic-procedure-scene-feature-value storing section 155a in the memory 155.

The endoscopic-procedure-scene classifying section 153 stores information concerning endoscopic procedure scenes classified over time (in time order), for example, by an appropriate number of frames (in the past from an image of a present frame) in a classified-scene storing section 155b in the memory 155.

When determining that reliability of the endoscopic procedure scene classified by the endoscopic-procedure-scene classifying section 153 is low, the endoscopic-procedure-scene-reliability determining section 153a sends, to the target-compression-ratio deciding section 154, a classification result of the endoscopic procedure scene classified by the endoscopic-procedure-scene classifying section 153 and stored in the classified-scene storing section 155b in an image (a signal) of a frame preceding, by a predetermined period, an image (a signal) of a frame, reliability of which is determined as low.

In an endoscopic procedure scene, reliability of which is not determined as low by the endoscopic-procedure-scene-reliability determining section 153a, the target-compression-ratio deciding section 154 decides a target compression ratio according to the classification result of the endoscopic procedure scene classified by the endoscopic-procedure-scene classifying section 153, the magnitude of the physical quantity, and the like. As explained above, the wirelessly transmittable data amount and the determination result are inputted to the target-compression-ratio deciding section 154. Therefore, the target-compression-ratio deciding section 154 decides the target compression ratio to set a data amount of a wirelessly-transmitted image signal within a range of a data amount equal to or smaller than the wirelessly transmittable data amount.

The target-compression-ratio deciding section 154 decides a target compression ratio referring to information stored in an LUT 156 prepared in advance. The image compressing section 154a compresses an image signal with a compression parameter corresponding to the target compression ratio decided by the target-compression-ratio deciding section 154 and sends the image signal to the wireless transmission section 24. The wireless transmission section 24 wirelessly transmits the image signal sent from the image compressing section 154a to the processor 3.

The other components are the same as the components in the first embodiment.

Figure 13:
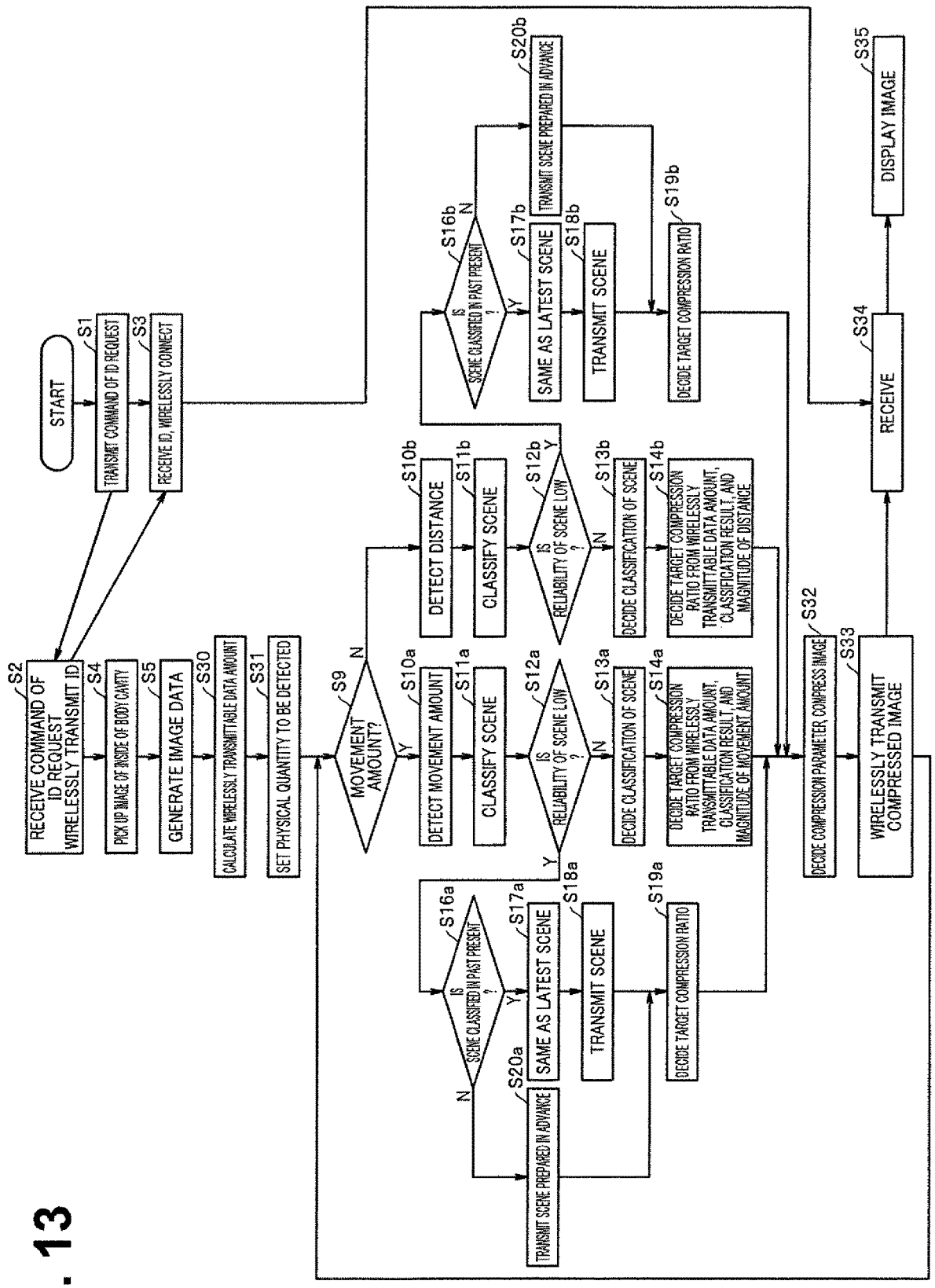
FIG. 13 is a flowchart showing processing contents of the wireless endoscope and a processor in the endoscope system according to the modification of the first embodiment.

Operation in the modification is as shown in FIG. 13. The operation shown in FIG. 13 is similar to the operation shown in FIG. 9. Therefore, the operation is briefly explained.

When an operation of the endoscope system according to the modification is started, as in the case of FIG. 9, the wireless endoscope 2I performs the processing in steps S1 to S3 and further performs the processing in steps S4 and S5. In next step S30', the image processing section 23B calculates a wirelessly transmittable data amount. For example, the wireless endoscope 2I wirelessly transmits, to the processor 3, a plurality of image data with a rate of a transmission data amount changed and the processor 3 receives a reception result. Consequently, the wirelessly-transmittable-data-amount calculating section 151a calculates a wirelessly transmittable data amount. The wirelessly-transmittable-data-amount determining section 151b determines that wirelessly-transmitted image data is within a range of the wirelessly transmittable data amount.

After the processing in step S5, in step S31, the wireless endoscope 2I (or the processor 3) performs processing for setting a physical quantity to be detected in order to use the physical quantity in endoscopic procedure scene classification and the like. When the wireless endoscope 2I is the 2A type, the control section 21 automatically sets the physical quantity to be detected to a movement amount. When the wireless endoscope 2I is the 2B type, the control section 21 may set a physical quantity detected by a not-shown operation switch or the like provided in the operation section 9 of the wireless endoscope 2I. Alternatively, the user may set the physical quantity to be detected beforehand from the user IF section 36 of the processor 3 and wirelessly transmit the physical quantity to be detected to the wireless endoscope 2I. The wireless endoscope 2I may set the physical quantity to be detected according to transmitted information.

In next step S9, the wireless endoscope 2I determines whether a movement amount is set as the physical quantity to be detected.

The wireless endoscope 2I performs the processing in steps S10a to S20a or steps S10b to S20b according to the determination processing in step S9. In the case of FIG. 9, the processor 3 performs the processing in steps S10a to S20a or steps S10b to S20b. However, in the modification, the wireless endoscope 2I performs the processing.

A target compression ratio is decided by the processing in steps S10a to S20a or steps S10b to S20b. In step S32, the compression-parameter deciding section 157 decides a compression parameter. The image compressing section 154a compresses an image using the decided compression parameter. In step S33, the wireless transmission section 24 wirelessly transmits compressed image data to the processor 3. After the processing in step S33, the wireless endoscope 2I returns to the processing in step S9.

In step S34, the processor 3 performs processing for expanding the received image data. An expanded image signal is outputted to the monitor 7. In step S35, the monitor 7 displays an endoscopic image. Note that processing for detecting both of a movement amount and a distance and wirelessly transmitting the image signal is the same processing as the processing shown in FIG. 11. However, step S8 before step S30 in FIG. 11 is changed to step S31 in FIG. 13. Step S15 after the processing in step S14 shown in FIG. 11 is changed to step S32 in FIG. 13.

According to the modification operating in this way, it is possible to set an appropriate target compression ratio and wirelessly transmit an image signal even when reliability in classifying an endoscopic procedure scene with respect to an image is low as in the first embodiment. When a transmission state of the wireless transmission is grasped, a wirelessly transmittable data amount is calculated, and an image signal in the case of a low target compression ratio is wirelessly transmitted, it is possible to set a target compression ratio of the image signal to be equal to or smaller than the wirelessly transmittable data amount and surely wirelessly transmit the image signal.

Note that, in the modification, when processing for deciding a target compression ratio in an image of one frame can be performed within one frame period, it is possible to perform processing for deciding a target compression ratio for each one frame period.

On the other hand, processing for deciding a target compression ratio in an image of one frame takes a plurality of frame periods, a target compression ratio only has to be decided in a cycle of the plurality of frame periods. In this case, an image picked up during the decision of the target compression ratio only has to be compressed using a (latest) target compression ratio, which is calculated immediately before the decision of the target compression ratio, and wirelessly transmitted to the processor 3 side. In the first embodiment and the like, only the movement-amount detecting section 52a or the distance detecting section 52b may be included as the physical-quantity detecting section 52.

Embodiments and the like configured by partially combining the embodiment or the modification explained above also belong to the present invention.

What is claimed is:
1. An endoscope system comprising:
an endoscope body configured to be inserted into a subject and including an image sensor provided at a distal end portion and a first wireless transmitter configured to wirelessly transmit an image signal detected by the image sensor; and a processor arranged on an outside of the subject and including a second wireless transmitter configured to receive a wirelessly-transmitted image signal, the processor being programmed to:

detect, in a state in which the endoscope body is inserted into the subject, a physical quantity reflecting a state in which the image sensor detects an image of the subject, the physical quantity being detected as movement amounts in a plurality of representative regions in an image for one frame on the basis of the image signal obtained by capturing an image of a region of the subject;

perform image processing of the wirelessly-transmitted image signal;

classify a scene of an image for observing the image of the region in the subject by the endoscope body based on (i) a current image signal obtained by capturing the image of the region in the subject with the image sensor, the captured image corresponding to an endoscopic procedure scene in a plurality of predetermined representative endoscopic procedure scenes, and (ii) feature values of the respective detected movement amounts in the plurality of representative regions in the captured image corresponding to the endoscopic procedure scene in the plurality of representative endoscopic procedure scenes;

determine a reliability of the classified scene; and in response to determining that the reliability of the classified scene is low, determine a target compression ratio of the current image signal wirelessly transmitted by the first wireless transmitter according to a classification result of a scene in a prior image signal of a frame preceding, by a predetermined period, a frame of the current image signal, which the reliability is determined as low.

2. The endoscope system according to claim 1, wherein the processor is programmed to:

detect, as the physical quantity, a plurality of distances between a plurality of positions in the subject from the captured image, and classify, based on feature values of the detected plurality of distances to the plurality of positions, the captured image corresponding to the endoscopic procedure scene in the plurality of representative endoscopic procedure scenes.

3. The endoscope system according to claim 2, wherein the processor is programmed to determine that the reliability of the scene is low when the detected plurality of distances to the plurality of positions vary to a value equal to or larger than a threshold in a local region or when an error amount of the plurality of positions, where the plurality of distances are detected, is as large as a value equal to or larger than a threshold.

4. The endoscope system according to claim 1, wherein the processor is programmed to:

act as (i) a movement detecting section configured to detect, based on the image signal obtained by capturing the image of the region in the subject with the image sensor, as the physical quantity, the respective movement amounts in the plurality of representative regions in the image for one frame, and (ii) a distance detecting section configured to detect, as the physical quantity, a plurality of distances between a plurality of positions in the subject, an image of the plurality of distances between the plurality of positions in the subject being captured by the image sensor; and classify, based on a detection result of at least one of the movement detecting section and the distance detecting section, the captured image corresponding to the endoscopic procedure scene in the plurality of representative endoscopic procedure scenes.

5. The endoscope system according to claim 1, wherein the processor is programmed to determine that the reliability of the classified scene is low when respective movement amounts in the plurality of representative regions vary to a value equal to or larger than a threshold in a local region or when an error amount of the plurality of representative positions, where respective movement amounts to be detected are detected, is as large as a value equal to or larger than a threshold.

6. The endoscope system according to claim 1, wherein the processor is programmed to classify, based on the features values of the detected physical quantity, the captured image corresponding to the endoscopic procedure scene in an insertion scene, a presence diagnosis scene, a qualitative and quantitative diagnosis scene, and a treatment scene serving as the plurality of representative endoscopic procedure scenes.

7. The endoscope system according to claim 1, wherein the processor is programmed to:

calculate a sum of squares difference between corresponding pixel values of blocks in the image; and determine a reliability of the classified scene based on a comparison of the calculated sum of squares differences of all blocks of the image.

* * * * *